United States Patent [19]
Saul

[11] Patent Number: 5,647,345
[45] Date of Patent: Jul. 15, 1997

[54] RESPIRATORY STIMULATOR & METHODS OF USE

[76] Inventor: Gilbert D. Saul, 27405 Puerta Real #130, Mission Viejo, Calif. 92691

[21] Appl. No.: 473,141

[22] Filed: Jun. 7, 1995

Related U.S. Application Data

[63] Continuation-in-part of Ser. No. 182,677, Jan. 14, 1994, abandoned, which is a continuation of Ser. No. 882,076, May 12, 1992, abandoned.

[51] Int. Cl.⁶ ................................................. A61M 16/00
[52] U.S. Cl. ............... 128/201.23; 128/720; 128/200.24
[58] Field of Search .......................... 128/201.23, 202.28, 128/200.24, 205.14, 261.13, 205.17, 720, 205.28, 203.28

[56] References Cited

U.S. PATENT DOCUMENTS

| | | |
|---|---|---|
| 603,021 | 4/1898 | Dight . |
| 733,027 | 7/1903 | Goldan . |
| 733,795 | 7/1903 | Goldan . |
| 743,294 | 11/1903 | Knowles . |
| 2,007,330 | 7/1935 | Hicks . |
| 2,241,535 | 5/1941 | Boothby et al. . |
| 2,284,053 | 5/1942 | Hermann . |
| 2,304,033 | 12/1942 | Shelton . |
| 2,893,387 | 7/1959 | Gongoll et al. . |
| 3,028,873 | 4/1962 | Kindred . |
| 3,097,642 | 7/1963 | Russell . |
| 3,208,449 | 9/1965 | Bartlett, Jr. . |
| 3,362,405 | 1/1968 | Hazel . |
| 3,395,699 | 8/1968 | Beasley . |
| 3,455,294 | 7/1969 | Adler et al. . |
| 3,513,843 | 5/1970 | Exler . |
| 3,827,432 | 8/1974 | Lundgren . |
| 3,859,997 | 1/1975 | Gandi . |
| 3,971,377 | 7/1976 | Damani . |
| 4,037,595 | 7/1977 | Elam . |
| 4,086,923 | 5/1978 | Henkin . |

(List continued on next page.)

FOREIGN PATENT DOCUMENTS

| | | |
|---|---|---|
| 1267471 | 9/1960 | France . |
| 693795 | 2/1902 | Germany . |
| 571867 | 1/1973 | Switzerland . |
| 27450 | 12/1904 | United Kingdom . |

OTHER PUBLICATIONS

Cottrell JJ. Lebovitz BL. Fennell RG. Kohn GM. Inflight Arterial Saturation:Continuous Monitoring by Pulse Oximetry. Aviat. Space Environ.Med. 1995: 6: 125–30.

Hubert V. Foster & Lawrence G. Pan; The Role of the Carotid Chemoreceptors in the Control of Breathing During Exercise; pp. 328–336+3. 1993.

Section 5/ Respiration—pp. 554–556 & Pulmonary Gas Exchange—Chapter 38—pp. 554–557.

K. Wassereman, et al. Lea & Febiger. Philadephia, 1987. Principles of Exercise Testing and Interpretation Glossary—pp. 239, 243, &21.

Mancini, D. M. —Uniique Identifier—p. 1—Benefit of Selective Respiratory Muscle Training on Exercise Capacity in Patients with Chronic Congestive Heart Failure.—Circulation 91(2) 1995 Jan. 15.

(List continued on next page.)

*Primary Examiner*—Vincent Millin
*Assistant Examiner*—William J. Deare, Jr.
*Attorney, Agent, or Firm*—John J. Connors; Connors & Assoc.

[57] ABSTRACT

Disclosed is an isocapnic respiratory stimulator for providing a mixture of fresh air and CO2 enriched exhaled air. The respirator comprises a mixing chamber with a breathing port and at least one vent port. Fresh air is mixed thoroughly with exhaled air in the mixing chamber. Upon sustained breathing from the chamber, the minute ventilation of the insure is increased with experiencing any substantial change in arterial blood CO2 level. This provides methods to avoid or treat hypoxia experienced by an individual at altitudes above 5000 feet, to treat carbon monoxide poisoning, to induce losing weight, to assist in smoking cessation, to condition an athlete to minimize dyspnea, and to condition respiratory muscles.

10 Claims, 6 Drawing Sheets

U.S. PATENT DOCUMENTS

| | | |
|---|---|---|
| 4,114,608 | 9/1978 | Russo . |
| 4,192,301 | 3/1980 | Hardwick . |
| 4,259,747 | 4/1981 | Taesler et al. . |
| 4,275,722 | 6/1981 | Sorensen . |
| 4,301,810 | 11/1981 | Belman . |
| 4,334,533 | 6/1982 | Henkin . |
| 4,373,522 | 2/1983 | Zien . |
| 4,508,116 | 4/1985 | Duncan et al. . |
| 4,628,926 | 12/1986 | Duncan et al. . |
| 4,919,132 | 4/1990 | Miser . |
| 5,039,035 | 8/1991 | Fitzpatrick . |
| 5,052,384 | 10/1991 | Kaneko . |
| 5,121,745 | 6/1992 | Israel ................................ 128/202.28 |
| 5,154,167 | 10/1992 | Hepburn . |
| 5,165,393 | 11/1992 | Kawaguchi . |
| 5,193,529 | 3/1993 | LaBaere . |

OTHER PUBLICATIONS

Smejkal, V. —Unique Identifier—p. 1—The Function of Respiratory Muscles in Healthy Persons During Tube Breathing (Czech)—Casopis Lekaru Ceskych 133(12)—1994 Jun. 13.

RELATIONSHIP OF HYPERPNEA CAUSED BY MUSCULAR EXERCISE TO THAT CAUSED BY INCREASED ALVEOLAR $PCO_2$. (FROM GUYTON AC. TEXTBOOK OF MEDICAL PHYSIOLOGY 6th Ed. PHILADELPHIA: W.B. SAUNDERS Co. 1981: 524.)

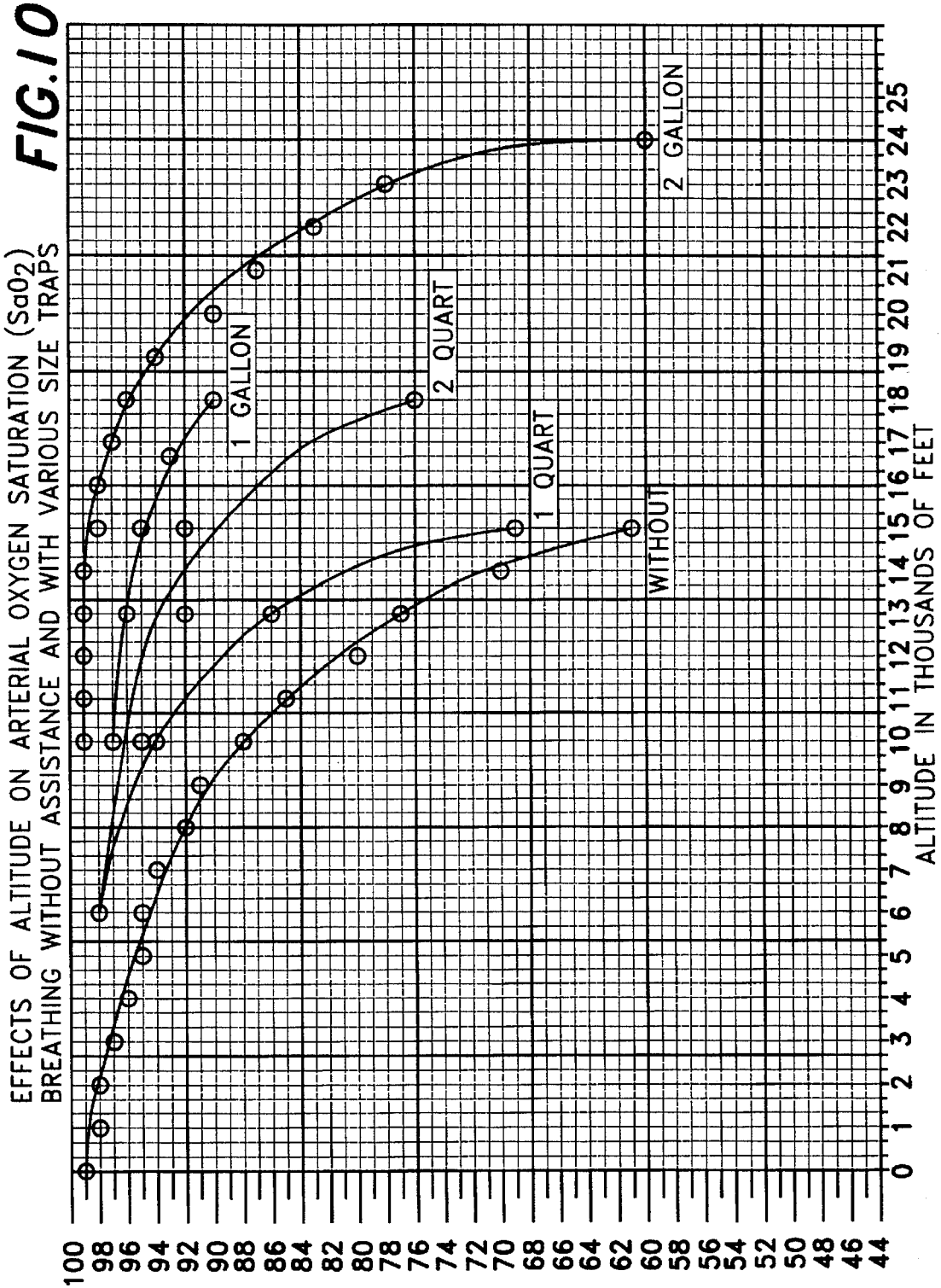

RESPIRATORY STIMULATOR & METHODS OF USE

RELATED PATENT APPLICATION

This application is a continuation-in-part application of U.S. Ser. No. 08/182,677, entitled "Non-Wasting Respiratory Stimulator and High Altitude Breathing Device," filed Jan. 14, 1994, now abandoned, which is a continuation application of U.S. Ser. No. 07/882,076, entitled "Non-Wasting Respiratory Stimulator and High Altitude Breathing Device," filed May 12, 1992, now abandoned, both of which are incorporated herein by reference and made a part of this application.

BACKGROUND OF THE INVENTION

1. Field of the Invention

The present invention relates to respiration devices, and, more particularly, to a simplified rebreathing device for ambulatory use which employs a carbon dioxide trap where exhaled air and fresh air are mixed to provide stimulation of respiration, greatly increased alveolar minute ventilation, and the equivalent of instant high altitude acclimatization.

2. Definitions

The following definitions are provided to enhance understanding of the concepts relating to the physiology of respiration:

Acapnia: A marked diminution in the amount of carbon dioxide ($CO_2$) in the blood.

Apnea: Cessation of respiration. True apnea is the absence of respiratory movements owing to acapnia and the consequent lack of stimulus by $CO_2$ to the respiratory center.

Alveolar Air: Air in the depths of the lungs which is more or less in contact with the respiratory epithelium, and can thus carry out gaseous exchanges with the blood.

Anoxia: no oxygen (O2).

Anoxic Hypoxia. Low partial pressure of O2 in the arterial blood due to interference with the oxygenation of the blood in the lungs, such as may result from a pulmonary abnormality or from a low tension O2 in the atmosphere.

Cheyne-Stokes Respiration: A type of breathing in which the respirations gradually increase in depth up to a certain point and then decrease; finally all respiration ceases for half a minute or so and then begins again as before.

Dead Space: The part of the respiratory tract possessing relatively thick walls, that is, from the nostrils to the terminal bronchioles, between which no gaseous blood interchange can take place.

Eucapnia or Eucapnic: The presence of $CO_2$ in normal amount in the blood.

Dyspnea: Shortness of breath.

Hypercapnia: The presence of CO2 in excess in the blood.

Hyperpnea or Hyperventilation: A condition in which the respiration is deeper and more rapid than normal.

Hypocapnia: A diminution in the amount of $CO_2$ in the blood.

Hypoxia: Low oxygen (O2),

Isocapnia: a state in which arterial CO2 remains constant.

Minute Ventilation: The tidal volume multiplied by the number of respirations per minute. For example, if a person inhales and exhales 12 times in one minute and his/her tidal volume is 0.5 liter, the minute ventilation is 6 liters per minute.

Partial Pressure: The pressure exerted by any one gas in a mixture of gases, equal to the pressure times the fraction of the total amount of gas it represents.

$PCO_2$: Abbreviation for partial pressure of carbon dioxide.

$PO_2$: Abbreviation for partial pressure of oxygen.

Q: Symbol for perfusion, the amount of blood perfusing the lungs. This amount equals the cardiac output (L/minute).

Tidal Volume: The amount of air that enters and leaves the lungs with each cycle of respiration. For example if a person inhales about 0.5 liters and exhales about 0.5 liters, the tidal volume is 0.5 liter.

V: Symbol for ventilation (L/minute).

V/Q: The ratio between ventilation and perfusion.

Vital Capacity: The greatest amount of air that can be expired after a maximal inspiratory effort.

BACKGROUND DISCUSSION

For more than a century, the role of carbon dioxide ($CO_2$) in protecting the oxygen ($O_2$) supply of brain and body has been recognized. For almost as long, investigators have known that $CO_2$ enriched air permits increased ventilation without hypocapnia. Under ordinary circumstances, each breath contains more than enough O2 to meet metabolic needs, as breathing supplies O2 and gets rid of CO2 formed in the body. But contrary to what might be expected, respiration is not driven by O2 lack but by CO2 excess. In fact, respiration is mediated by CO2 and the respiratory system is exquisitely sensitive to arterial CO2 levels. Thus, a slight increase in CO2 level will stimulate breathing, and a slight decrease in CO2 level will depress breathing. These respiratory responses maintain alveolar PCO2 and, hence, arterial PCO2 at nearly constant values.

A voluntary increase in the rate and depth of breathing causes CO2 to be exhaled at a faster rate than its rate of production by the body's metabolism and results in a drop in the amount of CO2 in the blood, i.e., results in hypocapnia. If vigorous, rapid breathing is continued for more than a few minutes, increasingly severe hypocapnia will cause cerebral vasoconstriction and unpleasant nervous system symptoms.

An increased rate and depth of breathing, or hyperpnea, without an appropriate increase in CO2 production from metabolism, can be voluntary or caused by a hyperventilation syndrome, anoxic hypoxia, or mechanical ventilation. In all cases, the resultant hypocapnia causes increasingly grave symptoms and is the limiting factor in the amount of excess ventilation that can be achieved. In a number of situations—a good example is the anoxic hypoxia that can occur in high altitude flying—a large increase in ventilation is desirable, and CO2 enriched air makes this possible.

Respiratory chemoreceptors respond to low arterial PO2, but this response tends to be sluggish and of low magnitude. However, if alveolar PCO2 is maintained by breathing CO2 enriched air, even mild anoxic hypoxia is an effective respiratory stimulant. With sudden exposure to severe hypoxia, such as loss of cabin pressure in an airplane at 25,000 feet, the hypoxic stimulus is strong enough to cause hyperpnea. However, this hyperpnea rapidly leads to hypocapnia which limits the respiratory response to a maximum of only about 65% above normal. The hypocapnia also causes cerebral vasoconstriction which further aggravates central nervous system hypoxia. Unless oxygen (or CO2 enriched air) is immediately available, the severe hypoxia within minutes will cause incapacitation or unconsciousness.

An acclimated mountain climber can do heavy physical work at high altitudes because the body can adapt to hypocapnia. This adaptation permits greatly increased ventilation which supplies enough O2 not only to prevent hypoxia at rest but also provides enough ventilation for strenuous climbing. However, this adaptive process does not always go smoothly, and acute mountain sickness is a common occurrence. At high altitudes, the alternating stimulation and inhibition of the respiratory center, first by hypoxia and then by hypocapnia, leads to Cheyne-Stokes respiration, which can become quite pronounced during sleep. In the apneic phase, severe hypoxia may potentially cause the subject to slip from sleep into coma, and sometimes from coma into death.

Many physicians, aware of the grave consequences of hypercapnia and CO2 narcosis, and accustomed to treating the anoxia of respiratory failure with O2 are likely to think of O2 as life giving and CO2 as a potentially dangerous exhalation. However, CO2 is just as essential in the body as O2. For example, CO2 is vitally important to maintain acid base balance, to maintain cerebral blood flow and, of course, to regulate breathing. During the 1920's, CO2 mixtures were frequently used to stimulate respiration in carbon monoxide asphyxia, and there was interest in its use in aviation, pilot anoxia being a major source of casualties in World War II.

Although early experiments with CO2 enriched air gave very encouraging results, technical limitations made direct blood gas data difficult to obtain. Without such information, the therapeutic use of CO2 was both unsubstantiated and hazardous. With the coming of aviation O2 and pressurized cabins in the 1940's, the problem of anoxia in high altitude flying was largely eliminated. This also eliminated the principle stimulus for the work on CO2.

Recently, however, various works have pointed out the similarity between the symptoms of acute mountain sickness (AMS) and carbon monoxide poisoning. Climbers obtained striking relief from symptoms of AMS with inhalation of 3% CO2 and commentators have suggested that this might be a useful emergency treatment for AMS. Also, over 50 years ago, studies showed that headache and other acute neurological symptoms in carbon monoxide poisoning were rapidly relieved by breathing a CO2 mixture, and that the benefit achieved by this means was greater than that produced by 100% O2 alone.

Yet, the promise of CO2 is still largely unfulfilled as CO2 enriched air is essentially unavailable in aviation, mountaineering, and medicine. The probable reason for this is that breathing CO2 mixtures is neither safe nor simple. One cannot just hook up a tank of CO2 to a breathing apparatus and expect to adjust the flow by monitoring its effect on respiration. To do so would be to risk almost instantaneous unconsciousness, potentially soon followed by brain damage or death. Producing a smooth flow of accurately mixed CO2 and air requires a sophisticated mixing device, both delicate and expensive.

Commercially prepared custom mixes of medical grade air and CO2 are available, but costly, the tanks very heavy, and breathing duration time quite limited. Even a group of experienced physician scientist mountain climbers who rediscovered the value of CO2 in treating acute mountain sickness, although they recommended 3% CO2 as a useful emergency treatment, did not feel that CO2 was a practical solution to the hypoxic problems of mountain climbing.

Various attempts to utilize exhaled air, which is high in CO2, have been made as a substitute for providing prepared custom mixes of CO2 and air. In fact, generations of emergency room physicians have had patients breathe into simple kraft paper bags to treat hyperventilation that can result from anxiety, fear, or trauma. The paper bag enables a hyperventilating patient to conserve and rebreathe exhaled air, thereby increasing the concentration of CO2 in the inhaled air. This, in turn, raises the CO2 content of the blood and relieves symptoms caused by low blood CO2. A normally ventilating individual who breathes into a paper bag will also experience an increase in blood CO2 which will markedly stimulate respiration.

This is the seminal idea behind all of the prior state of the art rebreathing inventions. In one fashion or another they are all designed to duplicate the function of a simple paper bag. However, breathing into a paper bag results in 100% wasted ventilation. Within a relatively short time, the CO2 concentrations rise and O2 concentrations fall to intolerable levels. In order to achieve a steady state, some fresh air must be added. It should be emphasized that the portion of ventilation that is supplied by the bag does nothing to improve alveolar ventilation and is therefore wasted.

The following devices are all variations on a simple paper bag. U.S. Pat. No. 2,304,033 to Shelton for a sanitary rebreathing bag is a paper bag, but modified with tubes attached to the bag. U.S. Pat. No. 2,007,330 to Hicks for a self administering carbon dioxide apparatus describes an inflatable nose/mouth mask connected by a tube to an inflatable rubber bag. U.S. Pat. No. 3,513,843 to Exler for a respiratory device for rebreathing CO2 consists of a nose/mouth mask connected to an inflatable sack, of readily variable size to adjust the same to the rebreathing capacity of the user, with an adjustable two-way flow breather valve and a one-way outlet valve. U.S. Pat. No. 4,192,301 to Hardwick for a rebreathing apparatus is a disposable, flexible polymer bag attached to a nose/mouth mask and an air control valve located between the mask and the disposable bag which is said to adjust the ratio of rebreathed air to fresh air through a fresh air inlet.

Ventilation can also be wasted and higher CO2 concentrations achieved by breathing through a long tube. Whatever the volume contained in the tube, an equal volume of ventilation will be wasted. In other words, the entire volume of air in the tube must be inhaled before the user can begin to get any fresh air. If the volume of the tube exceeds the vital capacity of the user, then ventilation is completely wasted and the situation is identical to that of breathing into a closed bag.

The following devices are all variations on a breathing tube. U.S. Pat. No. 3,455,294 to Adler is a respiratory device to increase the depth and volume of respiration in patients by adding a volume of dead space through which the patient rebreathes. The device comprises a multi-walled chamber of about 1 liter volume providing a tortuous pathway between a mouthpiece and exterior air. Thus, it is the equivalent of breathing into a long tube. The disadvantage of this device is that, during operation, the entire one liter volume in the tortuous pathway is filled with exhaled air containing CO2, and is rebreathed by the user without any mixing of fresh air with the exhaled air. The user is able to breath in fresh air only after breathing the entire one liter volume contained in the device, which can only be accomplished once breathing is stimulated and the user's tidal volume exceeds one liter. Moreover, even when tidal volume exceeds one liter, fresh air is never mixed with the exhaled air within the device; rather, if mixing occurs at all, it occurs in the lungs. U.S. Pat. Nos. 4,508,116 and 4,628,926, both to Duncan for a carbon dioxide rebreathing apparatus, are also generally of the same type as Adler, providing air baffles and chambers that provide a long air passage, again the equivalent of breathing through a tube.

U.S. Pat. No. 4,275,722 to Sorensen discloses a respiratory exerciser and rebreathing device which, through a system of valves, provides for an inhalation chamber and an exhalation chamber, with a sliding mechanism to vary the amount of air rebreathed from the exhalation chamber. This device has a complex network of chambers, valves and mechanisms, all designed to route exhaled air through an exhalation chamber and through an inhalation chamber that removes moisture from the exhaled air before inhaling. The exhalation chamber is widely open to ambient air so that fresh air is available at the bottom. Nevertheless, little or no turbulence and essentially no mixing occurs at the boundary layer between the exhaled air and ambient air other than by relatively slow diffusion. Although the patent at times refers to the exhalation chamber as a mixing chamber, there is essentially no mixing of ambient air with exhaled air in the device. Thus, this complicated device is essentially another long tube and wastes ventilation. It does nothing to improve alveolar ventilation and could never serve as a substitute for breathing oxygen at high altitudes. In addition, this device is unnecessarily complex and is disadvantageously expensive to manufacture, and in turn would be costly to purchase.

The prior art devices clearly mimic the effect of breathing CO2 enriched air in as much as they increase blood CO2 and stimulate respiration. However, this increased respiration does not improve alveolar ventilation and is therefore wasted. For this reason these devices can not be substituted for breathing CO2/air mixtures in high altitude applications and in most medical uses. A relatively simple low-cost device which mixes and utilizes CO2-containing exhaled air is therefore preferred. Consequently, there remains a need for a simple rebreathing apparatus that provides an appropriate CO2/air mixture. Because CO2/air mixtures are expensive and impractical, and generally not readily available, their full medical potential has never been realized. However, the crucial condition that needs to be met is that such an apparatus must do more than just stimulate ventilation, it also has to increase alveolar ventilation. The present invention meets this requirement and realizes all of the applications of CO2/air mixtures. It is, however, superior to CO2 enriched air because it works on an entirely different physiological principle. It provides respiratory stimulation on a par with vigorous exercise, far greater than CO2 stimulated respiration, and without any change in arterial blood CO2 level.

SUMMARY OF THE INVENTION

It is the objective of this invention to provide an respiratory stimulator and method of stimulating ventilation of an individual without substantially altering the carbon dioxide level in the individual's arterial blood. Unlike simply breathing air enriched with carbon dioxide, which causes hypercapnia and only very moderate stimulation of ventilation, the present invention stimulates ventilation probably by the same physiologic mechanism as muscular exercise, at very high levels of minute ventilation.

The respiratory stimulator and method of this invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENTS," one will understand how the features of this invention provide its benefits, which include an increase in minute ventilation without a change in the normal level of CO2 in arterial blood, providing a simple way to avoid or treat hypoxia, to treat carbon monoxide poisoning, to induce losing weight, to assist in smoking cessation, to condition an athlete to minimize dyspnea, and to exercise respiratory muscles.

The first feature of the respiratory stimulator of this invention is that it includes a rigid mixing chamber in which exhaled air and is mixed with fresh air. The chamber does not vary substantially in volume in response to exhalation and inhalation of a user. Typically, the volume of the chamber ranges between 1.5 and 20 liters. The volume of the chamber is selected based on the desired minute ventilation to be achieved by the user. The shape of the mixing chamber is not critical. It can be almost any convenient shape: spherical, cuboid, box like, blimp shaped, or tank shaped. The mixing chamber should not, however, be lobulated, segmented, or otherwise constricted so as to interfere with proper mixing of gases inside the chamber.

The second feature is that the chamber has a breathing port which provides communication between the user and the mixing chamber. With exhalation, the exhaled air enters the chamber through the breathing port and turbulently mixes with the contents of the chamber. Most of the exhaled breathe, including carbon dioxide, is entrapped in the chamber and mixed with the contents of the chamber. The exhaled air/fresh air mixture in the chamber is drawn through the breathing port with the next inhalation into the lungs of the user. The carbon dioxide in the mixture stimulates the ventilation of the user. The breathing port creates a jet stream that turbulently mixes the contents of the chamber. The breathing port may be enlarged into an open end of a face mask that fits over the mouth, the mouth and nostrils, or the entire face of the user. In this case, the exhaled air from the mouth and/or nostrils creates the jet stream to provide the mixing force. In one embodiment of this invention, the face mask has a collapsed position for storage and an extended position when in use. The respiratory stimulator may include a breathing passageway structure for placing the breathing port in communication with the mouth or nostrils, or both, of the user. This breathing passageway structure preferably has a volume which is less than 500 cubic centimeters.

When the breathing port is configured to fit over the user's mouth, or mouth and nose, or entire face, there is no added dead space. However, when a mask and tube are used to connect the user to the breathing port, then the volumes enclosed in the mask and tube function as additional dead space which wastes ventilation. The mask used in a high altitude proof of concept flight, contained a measured volume of 240 cubic centimeters (cc). The 16 cm section of tubing connecting the mask to the breathing port contained an additional 65 cc for a total dead space volume of 305 cc. This 305 cc of added dead space was not noticeable to the user, although it must have limited the peak altitude performance of the trap to some degree. A four segment length of tubing 64 cm long contained 260 cc of volume. When this tubing was used with the above 240 cc mask for a total dead space of 500 cc, this still produced no effect discernible to the user when breathing into a large trap. Thus, probably up to 500 cc of mask and tubing dead space can be added without significantly affecting the performance of a mixing chamber. However, for very high altitude applications, dead space should be kept to a minimum. This 500 cc figure for acceptable dead space is actually very generous. A low volume mask should not contain more than 120 cc, and a 120 cm length of tubing with an inside diameter of 1.5 cm contains 212 cc for a total dead space volume of 332 cc. This apparatus would permit vigorous, unimpeded breathing. The tubing would be long enough to permit an athlete or patient some freedom of movement, or allow placement of the mixing chamber at almost any convenient location in a small plane or overhead in an airliner.

The third feature of this invention is a vent opening structure in the chamber. This vent opening structure may be one or more holes in the wall of the chamber which enables fresh air to be drawn into the chamber and the exhaled air/fresh air mixture exhausted from the chamber. The size of the vent opening structure is important. It must be sufficient large so that there is very little increase in pressure within the chamber upon exhalation and very little decrease in pressure within the chamber with inhalation. At most, the pressure within the chamber upon exhalation or exhalation does not change more than 15 centimeters of water either above or below ambient atmospheric pressure. The vent structure must also be sufficiently restrictive to create a jet stream of fresh air that is sucked into the chamber upon inhalation. This stream of fresh air creates turbulence within the chamber so that there is good mixing of the fresh air and the exhaled air. The breathing port and vent structure should be located to achieve proper mixing of inhaled and exhaled air. For example, if for some reason a T shaped tank was required, a logical location for the breathing port would be at the base of the T, with three smaller vents, one at the top of the T and one at the end of each arm.

Simply breathing into a long tubular structure does not achieve the desired mixing of exhaled air and fresh air. Turbulence must be created in the chamber. With good mixing inside the chamber, the chamber volume cannot be considered "dead space." That is, it does not simply add to the user's respiratory dead space and waste ventilation. Instead, the user will obtain roughly 50% fresh air with each breath even when the mixing chamber volume greatly exceeds the user's vital capacity. The user never has a problem obtaining oxygen. The mixing chamber, however, does make it difficult for the user's respiratory system to eliminate $CO_2$. In effect it trap $CO_2$. The user's minute ventilation must increase proportionately to the volume of the chamber in order to eliminate the same volume of $CO_2$ that is produced at resting minute ventilation. Remarkably the stimulator of this invention does not increase $CO_2$ in the arterial blood. It seems to depend on a similar, or the same, physiological mechanism that stimulates respiration during exercise. Strenuous exercise produces very high minute ventilations without a change in blood $CO_2$. Large volume chambers can stimulate ventilation to minute ventilation values ordinarily only seen with maximal exercise, at least double the maximum stimulation that can be produced with a $CO_2$/air mixture.

Assuming a constant metabolic rate, the same amount of $CO_2$ is eliminated each minute whether the user is at rest or breathing into various size chambers. Thus, as chamber size is increased, the same amount of $CO_2$ is spread over increasingly large minute ventilations. Consequently, the $PCO_2$ inside the chamber actually falls with progressively larger chambers. This is the exact opposite of what happens when breathing $CO_2$/air mixtures where the higher the minute ventilation the higher the percentage of $CO_2$ required. The calculated $PCO_2$ inside a 4 liter chamber (for a subject with a tidal volume of 500 cc and minute ventilation of 6 L/min) is roughly 3 mm Hg, or about 0.4% $CO_2$. For a 10 liter chamber it is about 1 mm Hg, or about 0.1% $CO_2$. Under these circumstances, a 4 liter chamber produces a ventilation of about 54 L/min and a 10 liter chamber about 126 L/min. This compares to $CO_2$/air mixtures of 2%, 4% and 6% $CO_2$ producing respiratory minute volumes in the range of 9, 16, and 31 L/min respectively. Because of the increased ventilation, the $PO_2$ inside a chamber is close to the $PO_2$ in the ambient air and alveolar $PO_2$ rises above normal.

It has been found that the cross-sectional area of the vent opening structure should range between 0.75 and 20 square centimeters. For the best turbulent mixing, the cross-sectional area of the vent opening structure should range between 1.75 and 5.0 square centimeters. In accordance with this invention, upon exhalation, a portion of the exhaled air/fresh air mixture in the chamber substantially equal to the volume of air exhaled by the user is exhausted to the atmosphere through the vent structure and, upon inhalation, fresh air substantially equal to the volume of air inhaled by the user is introduced into the chamber through the vent structure. The vent opening structure has a sufficiently large cross-sectional area to allow the exhaled air/fresh air mixture to flow freely out of the chamber as the user exhales into the chamber without substantially increasing the pressure within the chamber yet is sufficiently restrictive to promote turbulent mixing in the chamber of fresh air drawn into the chamber upon inhalation with the exhaled air/fresh air mixture in the chamber.

A round vent with a diameter of 1 centimeter or area of 0.79 cm2 causes peak pressures of 15 cm of water inside the tank on inhalation and exhalation. With this size vent there is a noticeable increase in the work of breathing which is somewhat uncomfortable. However, the degree of hypercapnia generated by this back pressure seems minimal, and breathing could probably be sustained for prolonged periods. A possible advantage to this small a vent might be to enhance respiratory muscle conditioning.

When the vent size is increased to 1.5 centimeter (cm) diameter or 1.77 cm2, peak pressures in the mixing chamber falls to +2.5 cm of water. With a 2.0 cm diameter or 3.14 cm2, the pressure fluctuations are +1.3 cm of water. With both the 1.5 cm vent and the 2.0 cm vent, there is no noticeable resistance to breathing. However, even though breathing seems completely free and easy, forceful jets of air are created which carry 3 or 4 feet in distance. With a 2.7 cm or 5.73 cm2 vent, peak mixing chamber pressure fluctuations are less than +0.5 cm of water, yet there is still a noticeable jet of air more than a foot away. With still larger vents, the pressure fluctuations are no longer detectable with a water manometer, nor are there noticeable jets of air. However, mixing chamber performance does not degrade until the vent becomes greater than 5 cm diameter or 19.64 cm2. Thus, the optimum size for a vent is probably between 1.5 and 2.5 cm diameter or 1.77 to 4.91 cm2. If more than one vent is used, the sum of their areas should fall within this range, 1.77 to 4.91 cm2.

The fourth feature is that the respiratory stimulator of this invention increases the minute ventilation of the user to a predetermined level substantially above the minute ventilation of user when breathing normally during resting. This is achieved without any significant change in the user's arterial carbon dioxide blood level. The size of the chamber is selected based on the desired increase in minute ventilation desired. Thus, said chamber has a predetermined capacity based on the desired predetermined level of increased minute ventilation This invention also includes a method of stimulating ventilation of an individual without substantially altering the carbon dioxide level in the individual's arterial blood. This method comprises the individual breathing for a sustained period into a respiratory stimulator, the stimulator being in communication with the atmosphere, so that, upon exhalation, exhaled air is entrapped in the stimulator and, upon inhalation, a jet of fresh air is introduced into the stimulator to create turbulence within the stimulator to provide a mixture of exhaled air and fresh air which the individual breathes. Preferably, the mixing is accomplished solely by the user breathing into a mixing chamber in stimulator, with fresh air being drawn into the chamber as a jet stream upon inhalation and exhaled air being forced into the chamber to exhaust some of the exhaled air/fresh air mixture from the chamber without substantially increasing the pressure within the chamber. The surprising aspect of this method is that the minute ventilation of the individual increases yet the level of carbon dioxide in the arterial blood of the individual remains essentially constant. The chamber has a predetermined capacity based on the desired increase in the minute ventilation of the individual to a predetermined level substantially above the minute ventilation of the individual when breathing normally during resting. Typically, the minute ventilation of the individual may be increased to range between 24 and 200 liters per minute. When practicing this invention, the user is in a resting condition except for breathing into the chamber and the minute ventilation of the user increases to the same or even higher minute ventilation than the user can achieve during exercise. Consequently, the method of this invention effectively uncouples the ventilation of the user from metabolism of the user.

After an initial start up period, usually within about 5 to 10 minutes, the mixture of exhaled air and fresh air in the chamber comprises approximately 50% by volume exhaled air and approximately 50% by volume fresh air. The volume of exhaled air and the volume of fresh air in the chamber fluctuates as the individual breathes so that upon exhalation the amount of carbon dioxide in the chamber increases slightly above the 50% level, and upon inhalation the volume of fresh air increases slightly above the 50% level. Individuals may easily remain on the stimulator for a sustained period exceeding 24 hours.

The method may be employed to avoid or treat hypoxia experienced by an individual at altitudes above 5000 feet. At altitudes from about 5000 to 12,000 feet, many people experience hypoxia and this method provides a convenient way of treating this condition. At altitudes from about 12,000 to 24,000 feet oxygen is frequently employed to treat hypoxia. At these higher altitudes of from 12,000 to 24,000 feet, hypoxia can be treated without the need for oxygen using the method of this invention. The method of this invention may also be employed to treat carbon monoxide poisoning, to induce losing weight, to assist in smoking cessation, to condition an athlete to minimize dyspnea, and to condition respiratory muscles. Where the stimulator is connected between a mechanical ventilator and a patient, higher minute ventilations can be achieved. The present invention is particularly well-suited for a variety of aviation applications, as the stimulator may be substitute for oxygen in high altitude flying. The stimulator provides a large increase in minute ventilation for treating carbon monoxide poisoning. Moreover, the stimulator provides higher alveolar $PO_2$ for treating or preventing acute mountain sickness.

The present invention represents a substantial improvement over the prior devices, working on an entirely different principle from these prior devices. Consequently, it has several distinct advantages. It traps $CO_2$ in the mixing chamber, and breathing this trapped $CO_2$ effects physiological stimulation in a manner akin to exercise. The free mixing of fresh air with exhaled air in the chamber makes it possible for the respiratory system to maintain a normal alveolar PO2 and promotes increased ventilation comparable to the ventilation produced by exercise. The present invention increases alveolar ventilation and has all the high altitude and medical applications of CO2/air mixtures. None of the prior devices can function this way. Because the present invention stimulates ventilation to very high levels without changing the level of arterial $CO_2$ it is a vastly better respiratory exerciser than any of the prior devices. Because eucapnia is maintained, the device does not cause distress or discomfort and can be used for prolonged periods without loss of effectiveness or ill effects. The prior devices all stimulate ventilation by raising blood CO2 (i.e. by producing hypercapnia). This makes them both unpleasant and unsuitable for prolonged use.

The present invention also has substantial advantages over CO2/air mixtures contained in pressurized containers. It is lightweight, self contained, inexpensive, and the supply of CO2 in the chamber, being the user's own exhaled air, is unlimited. The exhaled air is breathed into the chamber, mixed with fresh air inhaled into the chamber, and rebreathed by the user. Because there is no fixed apparatus measuring the quantity of CO2 being supplied, there is no possibility of human error or equipment failure which may lead to accidental asphyxiation or CO2 narcosis. Because the stimulation provided by the stimulator does not cause hypercapnia as does breathing CO2 enriched air, the stimulation is much more physiological. The stimulator can produce stimulation akin to very vigorous exercise, double the amount that can be produced with CO2 enriched air.

The respiratory stimulator of the present invention provides an endless supply of a mixture of fresh air and exhaled air containing CO2. However, unlike the prior devices, the present invention utilizes an endless supply of exhaled air and fresh air, which are mixed together by the process of normal breathing, in which ventilation is not wasted. The chamber advantageously comes in a variety of different volumes, each having a specific volume which determines the increase in ventilation stimulated by the device.

The present invention is also advantageously simple to produce in a highly affordable form. Various embodiments of the present invention can also be provided to adapt to various uses, i.e., the device can be portably fastened to the user's nose and mouth area, or can be hooked up to an oxygen supply or adapted with a smog filter. The present invention can also be comprised of a collapsible housing to adjustably provide varying volumes for different users or for use at different altitudes. Moreover, the container of the present invention has applications in a number of settings, and should not be considered limited to the specific embodiments shown in the drawings or described herein.

The present invention also advantageously has a relatively large mixing chamber whereby fresh air is drawn into the chamber and is mixed with exhaled air by the turbulence caused by the introduction of air into the chamber. Turbulence is caused by inhaling, where fresh air is drawn into the chamber, and by exhaling, where exhaled air enters the chamber through the breathing port. When a face mask is used, the open end of the mask is the breathing port, and in this case, the breath from the user's mouth and nose causes the turbulence. Unlike the previous respiratory devices which require the user to inhale a volume of strictly exhaled air before any fresh air is breathed in, the present invention substantially mixes fresh air and exhaled air within the chamber prior to being inhaled. Substantial equalization of exhaled air and fresh air levels is achieved within the chamber after a relatively short amount of time as essentially equal amounts of fresh air and exhaled air enter the chamber with each breathing cycle. Simply put, the present invention is a breathing stimulator which makes possible the rebreathing of conserved or trapped, exhaled carbon dioxide, thus permitting hyperpnea without hypocapnia.

The present invention utilizes the mixing chamber, which upon exhaling is partially filled with CO2-containing exhaled air, and by inhaling can be partially filled with fresh air, as fresh air is introduced into the chamber through an opening to the atmosphere. The present invention thus comprises a CO2 trap which makes it difficult for CO2 to leave, but readily allows fresh air and O2 to be drawn into the trap as the user inhales. No costly valves, multiple chambers or other mechanisms are needed.

BRIEF DESCRIPTION OF THE DRAWING

The preferred embodiments of this invention, illustrating all its features, will now be discussed in detail. These embodiments depict the novel and non-obvious device and method of this invention as shown in the accompanying drawing, which is for illustrative purposes only. This drawing includes the following Figures (FIGS.), with like numerals indicating like parts:

FIG. 10 is a graph showing the effect of altitude on arterial oxygen saturation (SaO2). breathing unassisted and using various sized chambers.

DETAILED DESCRIPTION OF THE PREFERRED EMBODIMENTS

Figure 1:
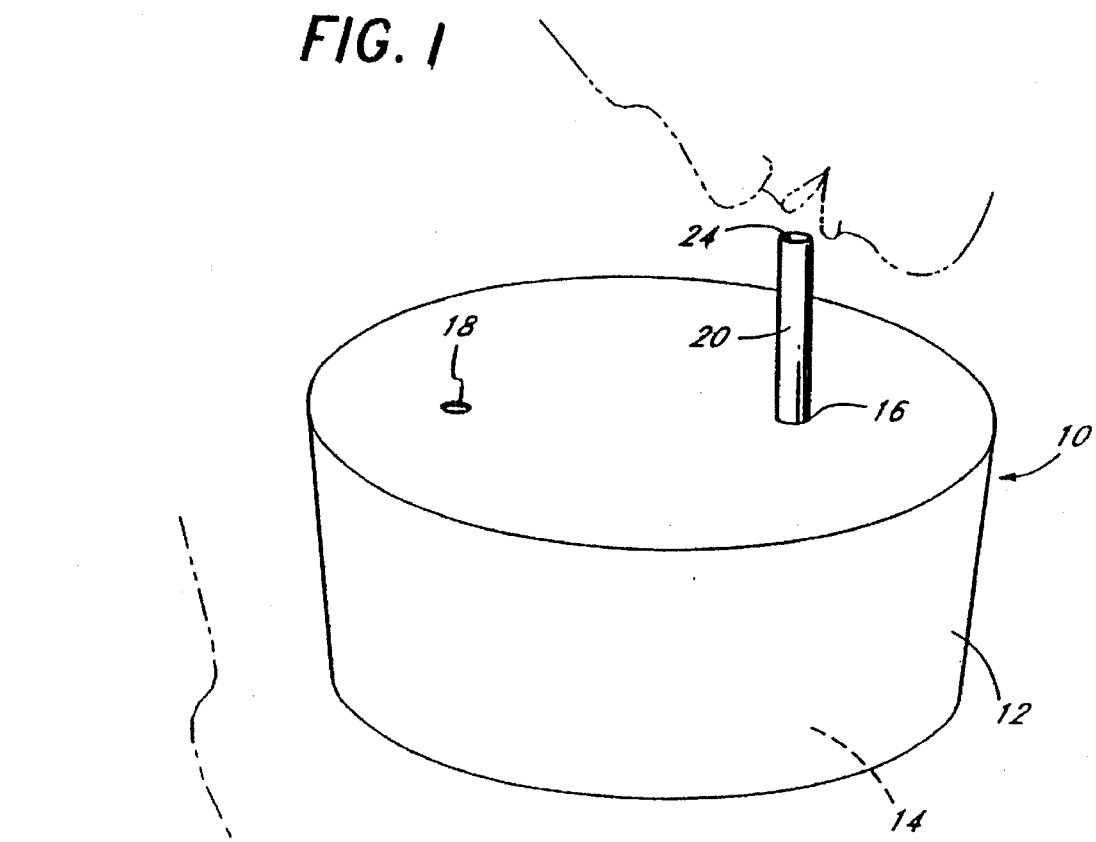
FIG. 1 is a perspective view of a rebreathing device of the present invention.

Referring to FIG. 1, there is disclosed a breathing device 10 which comprises a housing 12 having a mixing chamber 14 therein. Mixing chamber 14 is in gaseous communication with the exterior of the chamber by way of breathing port 16 and at least one vent port 18.

Figure 2:
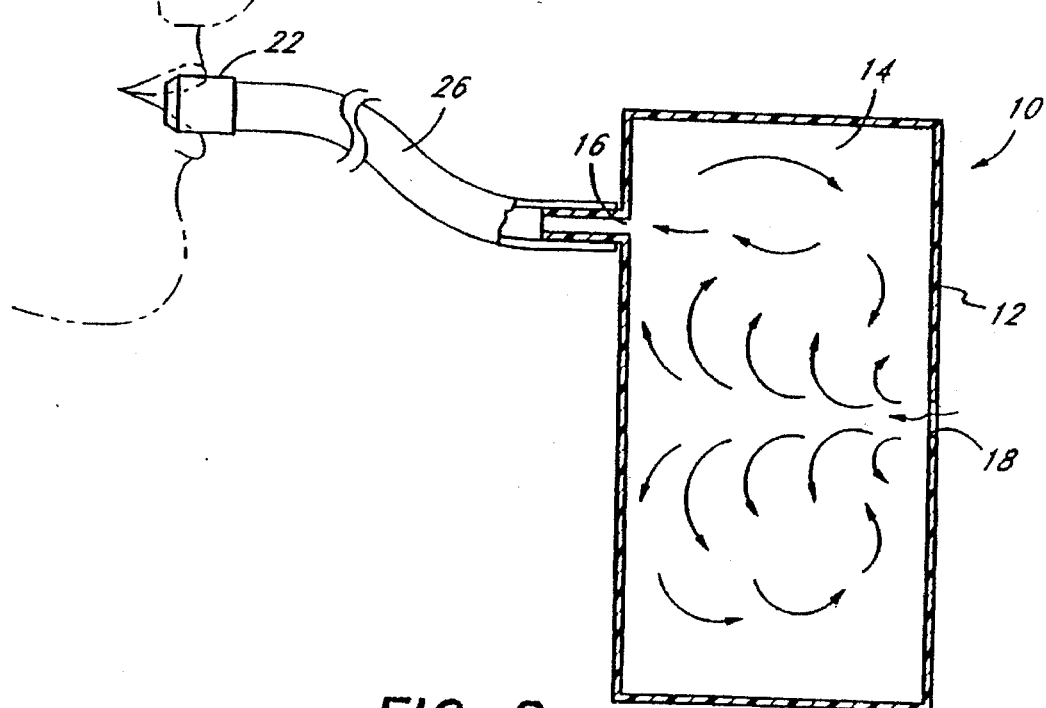
FIG. 2 is a cross-section of a rebreathing device of the present invention with a flexible tube and a mouthpiece.
Figure 4:
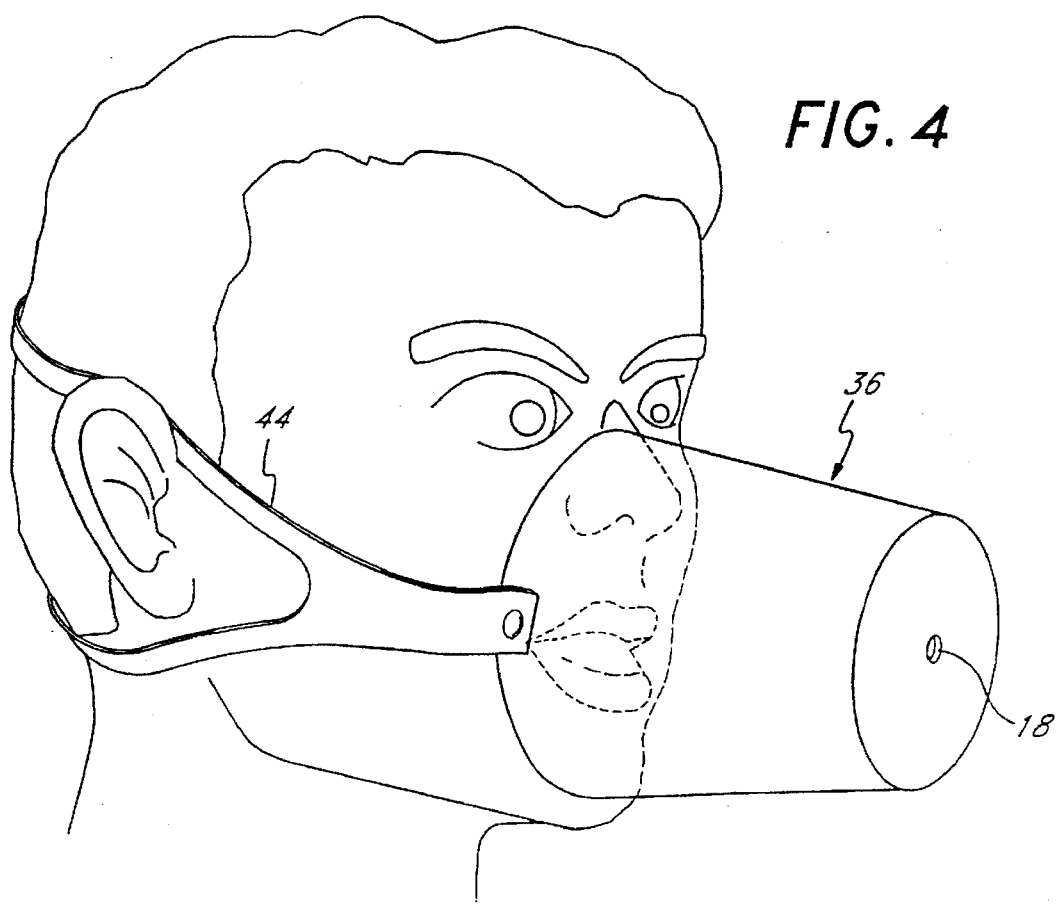
FIG. 4 is a perspective of a portable rebreathing device adaptable for use as a mask with a strap.

Preferably, breathing port 16 is provided with a fitting 20 such as a tubular connector for facilitating breathing. Any of the wide variety of fittings can readily be envisioned by one of ordinary skill in the art, depending upon the intended application of the breathing device 10. Preferably, the breathing fitting 20 is provided with a mouthpiece 22, as seen in FIG. 2, which may be in the form of a snorkel type mouthpiece. Alternatively, a breathing mask (not shown) covering the nose and mouth can be attached to the breathing fitting 20, providing a convenient way to use the device of FIGS. 1 and 2. The fitting 20 can also be mounted directly on the housing 12 with the proximal end of the fitting 24 extending outward. A flexible tubular extension 26, as shown in FIG. 2, can also be provided which allows for easy use. However, the residual air volume within any extension 26 will preferably be minimized, as will be apparent from the disclosure herein. A mask 36 can also be fitted over the face and held in place with straps 44 as shown in FIG. 4, or other suitable retention structures can be provided.

In reusable embodiments of the breathing device 10, the mouthpiece 22 or fitting 20 may be removably secured to the breathing port 16 of the housing 12, so that a one-time use disposable sterile mouthpiece (not shown) can be connected to the housing for each new user. Alternatively, a protective outer sheath (not shown) or other structure may be provided for removable attachment to the mouthpiece 22.

As will be apparent to one of skill in the art in view of the description contained herein, the volume between the breathing port 16 and the mouth of the user is optimally minimized in typical applications of the present invention. Since the volume contained in the fitting 20 is essentially an extension of the tracheal volume of the user, this additional dead space adds to the wasted volume of the system. Although for some applications such as athletic training, it may be desirable to artificially increase the wasted volume in the system, most applications of the present invention are optimized by minimizing the wasted volume.

Similarly, vent 18 preferably comprises an orifice without any additional tubular structures such as extensions. The preferred orifice is circular in configuration having a diameter of about 1,5 centimeters. This sized orifice allows fresh air to enter upon inhalation and a mixture of exhaled air and fresh air to be exhausted upon exhalation with only a slight change in the pressure in the chamber 14. Typically, the pressure in the chamber 14 does not vary more than about 2,5 centimeters centimeters of water either above or below ambient atmospheric pressure. The vent 18 is preferably of about the same cross sectional area as the breathing port 16, so that substantially equal flow characteristics are provided by the vent and breathing port. The vent is preferably relatively small so that when air is drawn into the chamber, a jet of air causing internal turbulence is created. The vent is preferably large enough, however, that air will flow freely out as the user exhales into the chamber. Vent 18 can alternatively take the form of a plurality of smaller ports or openings on the housing 12 for placing the chamber 14 in communication with the atmosphere. The vent 18 can be comprised of more than one opening, located to provide multi-directional turbulence which can facilitate mixing.

Figure 7:
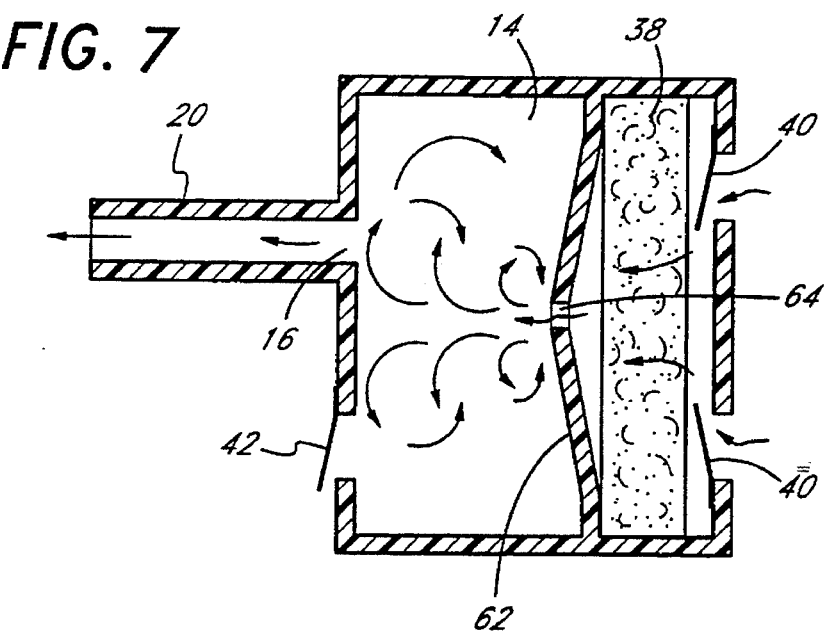
FIG. 7 is a schematic of a rebreathing device of the present invention with adaptable valves and a smog filter.

In another embodiment, the vent 18 is further provided with a mesh or filter 38, with one or more valves 40, as shown in FIG. 7, for preventing the introduction of unwanted airborne debris or atmospheric pollutants into the mixing chamber 14. One or more inlet valves 40 allows incoming air to pass through the filter 38 and into the chamber 14. The size and number of inlet valves are not critical, as long as air is permitted to flow freely into the mixing chamber. A funnel 62 with a small opening 64, which serves as an inlet vent, causes the incoming air to flow into the chamber as a jet of air, causing turbulence to facilitate mixing. Preferably, an outlet valve 42 allows air to bypass the filter and leave the chamber.

Any of the several one-way valves known to those skilled in the art can be provided, including flutter valves, and slit valves. Selection of any particular filtration element is largely dictated by the intended use environment of the breathing device 10, as will be apparent to one of skill in the art. In general, a simple gauze or mesh type filter is preferably used. Typically, the filter 38 will not introduce an unreasonable degree of resistance to air flow, unless resistance to air flow is desired such as in an application for breathing exercises. The porosity of the filter 38 adjustably determines the flow rate of the incoming air so that the size of the inlet valve 40 is not controlling of the flow.

Figure 8:
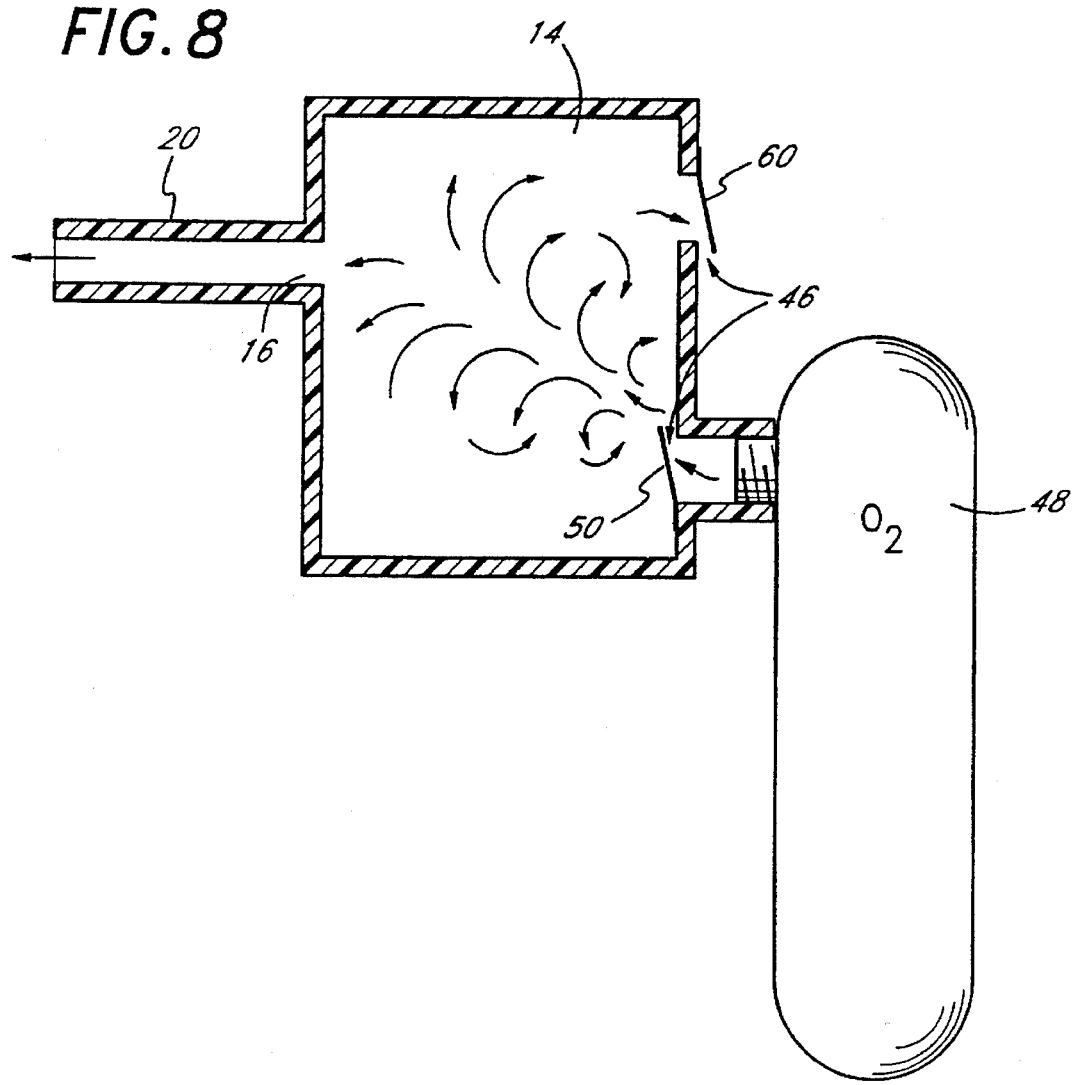
FIG. 8 is a schematic of a rebreathing device of the present invention with adaptable valves and an oxygen tank.

In another embodiment, as shown in FIG. 8, an oxygen supply can be attached to a two-way valve system 46 which allows pure O2 48 to be drawn in through an inlet valve 50, and excess air to leave through an outlet valve 60. A pressure regulator (not illustrated) will typically be used between the source of pressurized O2 and the mixing chamber, as is well known in the art. Pure O2 supplies 48 may be desirable in some medical applications.

In any of the single vent port embodiments or the multiple vent port embodiments discussed above, the vent or vents (not shown) can be located in a manner that optimizes mixing within chamber 14. For example, influent vents can be positioned tangentially on the periphery of a cylindrical housing 12 in a manner that induces a venturi flow within the chamber 14, causing a vortex flow circulation in the cylindrical housing. In one embodiment, the cylindrical housing can have a spiral exterior configuration with the vent 18 located on the wall extending along an axis generally parallel to the longitudinal axis of the cylinder. Influent into this spiral will be tangential, causing the flow to swirl around to maximize the mixing within the housing. Alternatively, one or more baffles (not shown) can be installed on the inside of the vent to focus or dissipate the flow of air tangentially into the housing. Preferably, for maximum circulation to occur within the chamber, the breathing port 16 should be substantially on the opposite end of the chamber from the vent 18. In general, however, chambers within the range of from about 1 liter to about 12 liter will likely exhibit sufficient mixing without regard to vent location.

Figure 3:
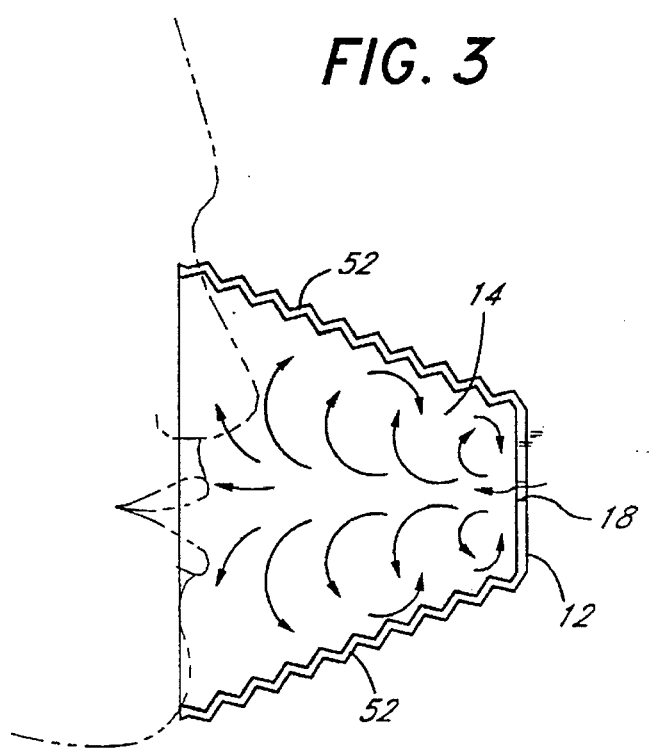
FIG. 3 is a schematic of a collapsible rebreathing device of the present invention in its open position.
Figure 5:
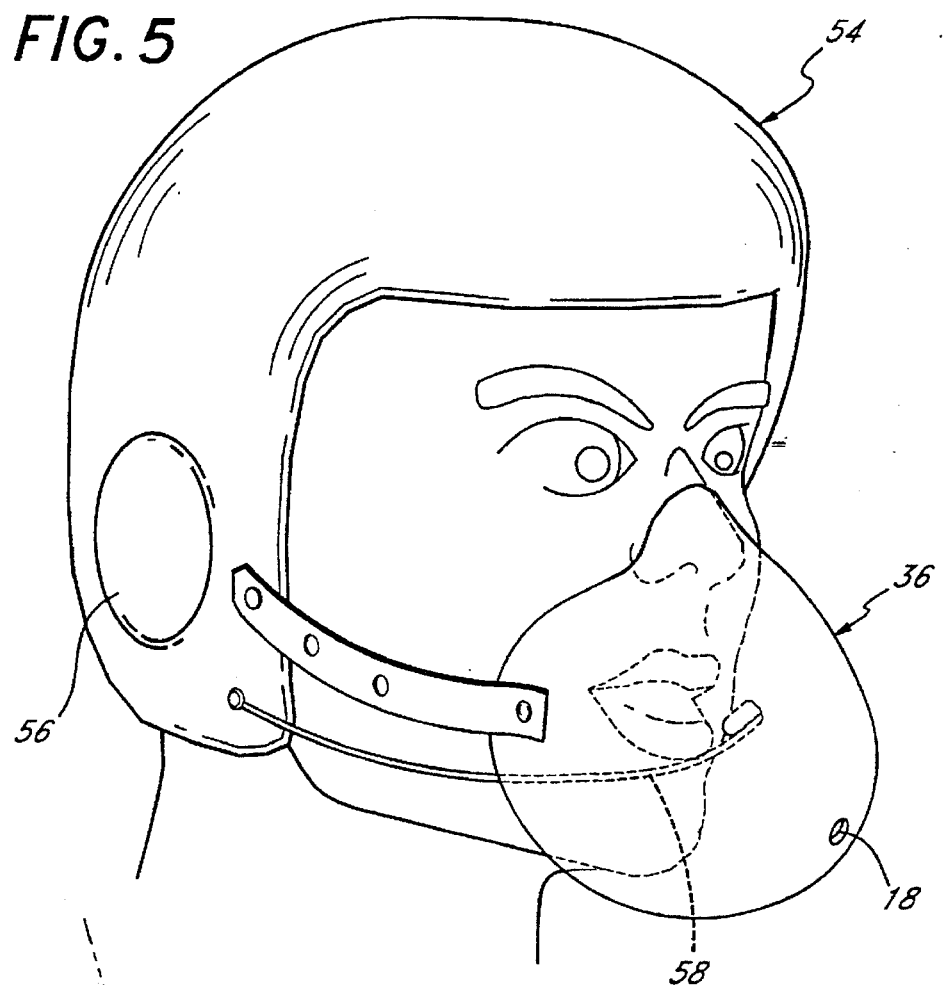
FIG. 5 is a perspective of a portable rebreathing device with a mask, helmet, headphones and a microphone.

The breathing port 16 can also be adapted to cause exhaled air to be introduced into the chamber 14 as a jet stream to facilitate mixing. The breathing fitting 20 can be positioned such that it directs exhaled air at a tangent to cause a vortex swirl within the cylindrical housing 12. Indeed, because people tend to exhale more vigorously than inhale, this process can be even more important to proper mixing. In the embodiment of FIGS. 3–5, the exhaled air comes directly from the nose and mouth of the user, which assumes the function of the breathing port, and the mixing is caused by the direct exhalation into the chamber.

For some applications, such as mechanical ventilation where the force of ventilation might be insufficient to produce good mixing, the inclusion of a fan (not shown) within the chamber would be advantageous. A probe (not shown) for measuring PCO2 levels may also be included in the chamber 14.

Figure 6:
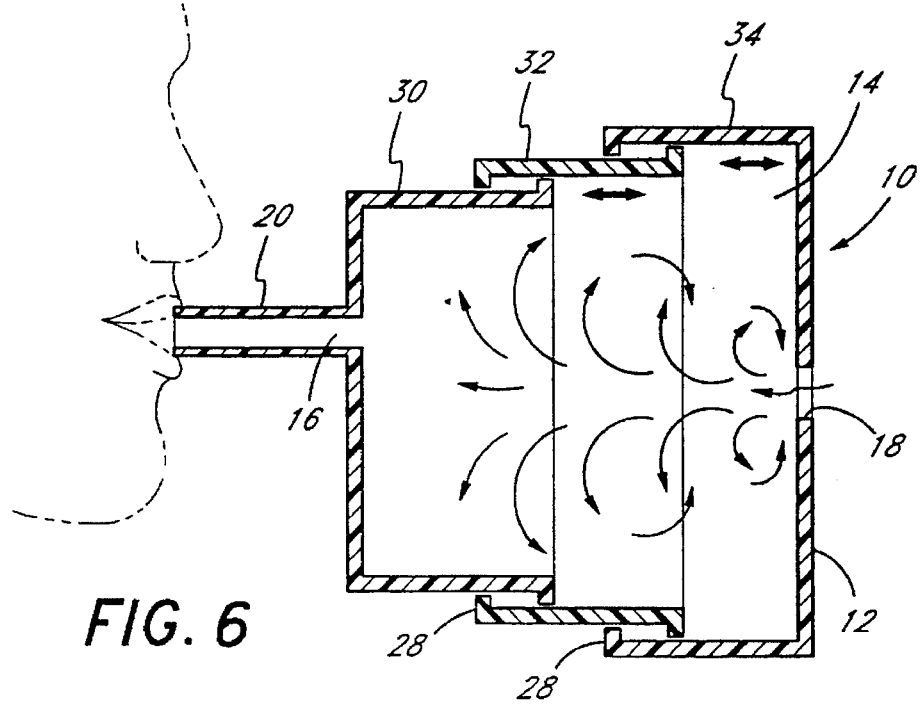
FIG. 6 is a schematic of a telescoping rebreathing device of the present invention in an intermediate position.

The volume of air in the mixing chamber 14 is preferably within range of from about 0.5 to about 20 liters, and, more preferably, within the range of from about 1.5 to about 10 liters. With a very small trap, such as a 0.5 L trap, the tidal volume is likely to be twice the volume of the trap. With such a small trap, a slight degree of hypercapnia may result, having an alerting effect which could be useful as an anti-drowsiness device. On the other hand, in a relatively large trap, with good mixing in the trap, the average content of the air in the trap will approach 50% exhaled air and 50% ambient air, and will substantially stabilize over time. Alternatively, housing 12 can be constructed in a manner which provides a selection of chamber volumes. For example, as can be seen in FIG. 6, housing 12 can be provided with a telescope type extension structure 28 wherein a first portion of the housing 30 is slidably concentrically fitted within a second portion 32 and/or third portion 34 of the housing and adapted to be displaced between a first position in which the chamber 14 has a first volume, and at least a second position in which the chamber 14 has a second volume. Alternatively, the housing 12 can be provided with a plurality of pleats 52 so that the chamber volume can be modified in an accordion-like fashion, as can be seen in FIG. 3. Optionally, a graduated scale (not shown) is provided to provide an indication of the volume of the chamber 14.

The breathing device 10 can be constructed in any of a variety of manners which will be readily understood by one of skill in the art in view of the disclosure contained herein. For example, in a fixed volume chamber 14, the housing 12 can be vacuum-formed, injected-molded, or produced in any of a variety of other manners well known in the art of thermoplastic or thermoset forming. Pre-molded plastic parts or plastic sheet stock can also be solvent bonded, heat bonded or bonded with adhesives. Alternatively, the housing 12 can be constructed from cold rolled or other metal sheet stock such as aluminum or stainless steel, to provide a sterilizable reusable breathing device.

Inexpensive disposable breathing devices can also be constructed from paper, cardboard or related materials, such as waxed board or other combinations or composites and layered light weight materials. Material choice and the use of a fixed volume chamber or collapsible housing are largely governed by the intended application of the device, and the available storage space for devices prior to use.

The volume of air in the chamber 14 functions as a carbon dioxide trap, in which exhaled air is trapped and mixed with ambient air being drawn in. The chamber 14 conserves and accumulates exhaled CO2 until the percentage of CO2 in the container reaches a level that stimulates respiration, which produces the minute ventilation determined by the volume of the trap. The actual minute ventilation required by the chamber 14 is a function of both resting tidal volume and resting minute ventilation and varies from one user to another. Minute ventilation must increase proportionally to the volume of the trap in order to exhale the same volume of CO2 that was contained in the resting minute ventilation. Because of the increased minute ventilation, the PO2 of air inhaled from the trap is virtually the same as that of inhaled ambient air. Chamber 14 makes it difficult to get rid of CO2 but does not interfere at all with the uptake of oxygen. It is thus a safe, simple, lightweight, portable, and stimulator which greatly increases alveolar ventilation and provides the equivalent of instant high altitude acclimatization The importance of providing proper mixing of incoming air 20 with exhaled air is demonstrated in Examples I and II below, which qualitatively compare the use of two rebreathing devices of the same volume, one ventilation wasting, the other entrapping exhaled CO2.

EXAMPLE I

Comparison of 3.87 Liter Wasting Rebreather With the Present Invention

A 1 gallon or 3.87 liter elongated container measuring 7×7×79 cm, with the vent end of the box open, was compared to an entrapping exhaled CO2 rebreather of the same volume and embodying the present invention. The degree of pulmonary ventilation or the level of blood CO2 was qualitatively estimated by measuring the length of time a breath could be held following use of each device. Short breath holding time is attributable to excessively high CO2 levels, while the ability to hold breath is promoted by increased alveolar ventilation and eucapnic CO2 levels.

The following results were obtained. The ventilation wasting device took about three minutes to achieve a stable maximum breathing rate of 28/min at near maximum tidal volume. At this point there were sensations of shortness of breath, blood pounding in the ears, and a pounding headache synchronous with the pulse. At five minutes there was a feeling of some confusion, and breathing was stopped at the end of an inspiration and breath-holding timed. Breath could only be held for 12 seconds. This compared to a breathholding time of 25 seconds after a period of quiet breathing. The extremely short breath-holding time produced by the ventilation wasting device is due to high blood CO2, and this is also the cause of the rapid breathing.

The identical protocol was followed using the stimulator of the present invention. After five minutes of breathing into the stimulator of the present invention, there were no unpleasant sensations. Respiration was 20/min and of moderate tidal volume. Breath-holding was 55 seconds, and this compared to 57 seconds after five breaths of approximately the same depth. The reason for taking five successive breaths was to thoroughly ventilate the lungs but not blow off so much CO2 as to produce a low blood CO2 which would markedly prolong breath-holding.

EXAMPLE II

Effect of 9.675 Liter Stimulator in Accordance with the Present Invention

A further comparison was made with a much larger stimulator in accordance with the present invention having a gas volume of 2½ gallons or 9.675 liters. This device took almost 10 minutes for breathing to reach a maximum rate and stabilize at 34/min with a tidal volume estimated at 4 liters. After 17 minutes there were no adverse symptoms, no sensation of shortness of breath, and no discomfort. Breath-holding was timed at one minute 50 seconds. This compared to only one minute 20 seconds after five similarly deep breaths. Though the device may have produced a slight degree of hyperventilation with lowered blood CO2 initially, this device produced a pulmonary ventilation of about 126 liters/min, more than 20 times the typical resting rate of 6 liters/min. It is quite impressive that this enormous ventilation caused no discomfort and could have been continued indefinitely.

The discomfort produced by ventilation wasting rebreathing devices should not be underestimated. The 3.87 liter device described above is probably at the upper limit of what can be tolerated in a wasting rebreather. But even much smaller volumes produce a sense of shortness of breath, unease and discomfort. In some individuals they can precipitate a full blown panic attack.

Examples III and IV will help explain how the carbon dioxide trap works. In both examples, the hypothetical subject is a vigorous male with the following respiratory parameters:

| | |
|---|---|
| Vital capacity | 4.8 liters |
| Tidal volume (rest) | 0.5 L |
| Respiratory rate at rest | 12/min |
| Respiratory minute volume (rest) | 6 L/min |
| Anatomical dead space | 150 ml |
| Alveolar ventilation (rest) | 4.2 L/min |
| Maximum voluntary ventilation | 150 L/min |
| $PH_2O$ (water vapor) in lungs | 47 mm Hg |
| $PO_2$ in airway before alveoli | 150 mm Hg |
| $PO_2$ in alveoli | 100 mm Hg |
| $PCO_2$ in alveoli | 40 mm Hg |

For the sake of simplicity, any increase in oxygen consumption (and $CO_2$ production) due to the work of increased ventilation will be ignored.

EXAMPLE III

The subject breathes into a long tube with a contained volume of 6.5 L. In order to obtain 0.5 L of pulmonary ventilation, he will have to increase his tidal volume to 7.0 L. Clearly, this is impossible since his vital capacity is only 4.8 L. No matter how fast or how deep the subject breathes, he will be unable to obtain any fresh air. If he does not abandon the effort, he will soon suffocate. This is truly wasted ventilation.

EXAMPLE IV

In this example, the subject now breathes into a 6.5 liter container which is open to the outside through a small hole. Inside the container is a fan that rapidly and completely mixes inhaled air with the air in the contained volume. Now the subject will obtain at least some fresh air with each breath, so the previous reasoning cannot be used to arrive at the new required tidal volume. However, because the minute ventilation is determined by how much carbon dioxide has to be eliminated, then it can be reasoned that the amount of $CO_2$ that was contained in 0.5 L will now be contained in 7.0 L (6.5 liters in container plus 0.5 liter tidal volume). Thus, to eliminate this amount of $CO_2$, the subject will once again have to increase his tidal volume to 7.0 L, exactly the same result as with the long tube. Once again, this will be an impossibility. However, the subject will be able to increase his per minute ventilation. Seven liters divided by 0.5 L equals 14, so if his resting ventilation of 6 L/min is multiplied by 14, this new minute ventilation of 84 L/min will eliminate the same amount of $CO_2$. A ventilation of 84 L/min is not much more than half his maximum voluntary ventilation, and he should be able to keep this up indefinitely. Thus, there is a world of difference between breathing into a long tube and breathing into a well circulating $CO_2$ trap.

In Example IV, a fan insured mixing of the air in the trap. As it turns out, a fan is not required. The turbulence produced by vigorous breathing adequately mixes new and old air in the trap. In an actual trial with a large trap, a plastic container with a measured volume of 6.8 L was used. Two widely spaced 2 cm diameter holes were drilled in the top of the container. One hole served as a vent, the other was fitted with a 1.5 cm internal diameter plastic breathing tube. This was used snorkel style in place of a mask.

It would seem probable that if a trap and a $CO_2$ mixture both produce the same degree of respiratory stimulation, they would both contain the same percentage of $CO_2$. If a 6% $CO_2$ mixture produces a ventilation of about 31.5 L/min and a 2.1 L trap also produces a ventilation of about 31.5 L/min, then the trap should contain 6% $CO_2$. Based on this reasoning it was anticipated that breathing into a 6.8 L trap would be quite challenging. It was thought the $PCO_2$ in the trap would be high enough to cause considerable hypercapnia.

Instead, breathing into the trap was surprisingly easy. As the $CO_2$ concentration gradually built up, respiration became deeper and faster. After about six minutes, respiration stabilized at about 28/min. Tidal volume was very high, estimated at over 3 L. Pulse rate went from a resting level of 50/min to 60/min. Breathing into the trap was continued for over 40 minutes with no change in pulse rate and only minor variations in tidal volume and respiratory rate. At no time were there any symptoms of hypercapnia: no headache, nausea, confusion or change in pulse rate. The subject felt no dyspnea and no fatigue and believed he could have kept breathing into the trap indefinitely. After stopping, there were no symptoms, specifically no onset of headache.

All of this was somewhat surprising. On page 532 of the physiology text by Ganong entitled "Review of Medical Physiology," published in 1981 by Lange, there are three graphs showing respiratory minute volume, tidal volume, and respiratory rate plotted against alveolar PCO2 with various $CO_2$/air mixtures. The highest $CO_2$ concentration used was 6%, and this produced a respiratory minute volume of about 31.5 L/min, a tidal volume of about 1.65 L, a respiratory rate of 19/min, and an alveolar $PCO_2$ of about 50 mm Hg. Of the three graphs, the one showing respiratory rate is the most linear. Extrapolating from this graph to a respiratory rate of 28 gives an alveolar $PCO_2$ of 74 mm Hg. If this were the case, the subject would have been severely hypercapnic. Some other mechanism must be involved.

There is a fundamental difference between breathing a $CO_2$ mixture and breathing into a trap. With a $CO_2$/air mixture the supply of $CO_2$ is unremitting and inescapable. With a trap, an increase in tidal volume or respiratory rate, immediately lowers the concentration of $CO_2$ in the chamber 14. This may permit the operation of a physiological mechanism that increases ventilation so as to keep arterial $PCO_2$ at a constant level. What takes place when breathing into a trap is closer to what actually occurs during exercise: there is a marked increase in ventilation even though arterial $PCO_2$ does not rise. This means that a trap is much more physiological than a $CO_2$ mixture. The stimulator of this invention produce far higher minute ventilations than can be achieved with $CO_2$/air mixtures. $CO_2$ produces only moderate stimulation. Mixtures of 2%, 4% and 6% $CO_2$ and air produce respiratory minute volumes in the range of 9, 16 and 31 L/min respectively. Normal alveolar $PCO_2$ is 40 mm Hg or 5.3% $CO_2$. When the percentage of $CO_2$ in the ambient air exceeds this amount hypercapnia is inevitable. The maximum minute volume that can be produced by $CO_2$ is about 68 L/min at an alveolar $PCO_2$ of about 64 mm Hg. Beyond this, respiration begins to fail from impending $CO_2$ narcosis (See FIG. 9). It is extremely unpleasant to breath these high concentrations of $CO_2$, and most people can only tolerate them for a few minutes.

Table I illustrates the linear relationship between trap size and required minute ventilation, as well as the improvement in alveolar ventilation that occurs even with small volume traps. The table is not based on data. The values have been calculated on the basis of some assumptions. The assumptions are as follows: (1) resting respiration is 6 L/min with a tidal volume of 0.5 L at a rate of 12/min, resting alveolar ventilation is 4.2 L/min, and dead space is constant at 150 cc; (2) arterial $PCO_2$ is maintained at a normal 40 mm Hg; (3) there is good mixing in all traps and the use of average values of partial pressures is justified; (4) there is no increase in metabolism with increasingly energetic breathing. (This is obviously not the case, but because breathing is so efficient, the increase in $CO_2$ production is probably negligible with small and medium sized traps. With large traps it is not, but the only effect is to make the trap seem even larger than it is.)

Minute Ventilation Required by Trap

As described above, the minute volume that a particular trap will produce is determined by the need to blow off a specific amount of CO2 every minute. This is calculated from the formula:

Minute Ventilation=(trap volume+0.5 $L$)×12/min

PO2 of Inhaled Air

The $PO_2$ of the air inhaled from a trap (the $PO_2$ in the airway after the $PH_2O$ has reached 47 mm Hg) is calculated thus. At rest, the $PO_2$ in 350 ml of alveolar ventilation goes from 150 to 100 mm Hg with each 0.5 L respiration. This 50 mm Hg is then spread over an additional 150 cc of dead space air, to make up the tidal volume of 0.5 L. Thus, the ratio 350 cc/500 cc×50 mm Hg=35 mm Hg, gives the drop in $PO_2$ in each 0.5 L of resting tidal volume. In turn, the ratio 0.5 L/(trap volume+0.5 L)×35 mm Hg subtracted from 150 mm Hg (the $PO_2$ of ambient air after it is saturated with 47 mm Hg of water vapor)=the $PO_2$ of the air inhaled from the trap.

PO2 Inhaled Air in mm $Hg$=150 mm $Hg$ minus 0.5 $L$/(trap volume+0.5 $L$)×35 mm $Hg$

PCO2 of Inhaled Air

The $PCO_2$ in the air inhaled from the trap is calculated as follows. The $PCO_2$ in 350 cc of resting alveolar ventilation goes from 0 to 40 mm Hg. Thus, 350 cc/500 cc×40=28 mm Hg, the $PCO_2$ in each 0.5 L of resting tidal volume. Thus, 0.5 L/(trap volume+0.5 L)×28 mm Hg=$PCO_2$ of air inhaled from the trap.

PCO2 inhaled air in mm $Hg$=0.5 $L$/(trap volume+0.5 $L$)×28 mm $Hg$

Alveolar PO2

The alveolar $PO_2$ is calculated as follows. The ratio 0.350 L/(trap volume+0.35 L)×50 mm Hg=drop in alveolar $PO_2$. This, subtracted from the previously calculated $PO_2$ of air inhaled from the trap gives the alveolar $PO_2$.

Alveolar $PO_2$ in mm $Hg$=$PO_2$ Inhaled Air Minus 0.35 $L$/(trap volume+0.35 $L$)×50 mm $Hg$.

Alveolar PCO2

The alveolar PCO2 is calculated as follows. The ratio 0.350 L/(trap volume+0.35 L)×40 mm Hg=increase in alveolar PCO2. This, added to the previously calculated PCO2 of the air inhaled from the trap gives the alveolar PcO2.

Alveolar $PCO_2$ in mm $Hg$=PCO2 Inhaled Air Plus 0.35 $L$/(trap volume+0.35 $L$)×40 mm $Hg$.

TABLE I

| Trap Vol in L | Min Vent in L/min | PO2 Inhaled Air | PCO2 Inhaled Air | Alv PO2 mm Hg | Alv PCO2 mm Hg | Art PCO2 mm Hg |
|---|---|---|---|---|---|---|
| None | 6 | 150 | 0 | 100 | 40 | 40 |
| 1.5 | 24 | 141 | 7 | 132 | 15 | 40 |
| 2.0 | 30 | 143 | 6 | 136 | 12 | 40 |
| 2.5 | 36 | 144 | 5 | 138 | 10 | 40 |
| 3.0 | 42 | 145 | 4 | 140 | 8 | 40 |
| 4.0 | 54 | 146 | 3 | 142 | 6 | 40 |
| 5.0 | 66 | 147 | 3 | 144 | 6 | 40 |
| 6.0 | 78 | 147 | 2 | 144 | 4 | 40 |
| 8.0 | 102 | 148 | 2 | 146 | 4 | 40 |
| 10.0 | 126 | 148 | 1 | 146 | 2 | 40 |
| 12.0 | 150 | 149 | 1 | 148 | 2 | 40 |
| 15.0 | 186 | 149 | 1 | 148 | 2 | 40 |
| 20.0 | 246 | 149 | 1 | 148 | 2 | 40 |

Note: Table I does not represent data. Numerical values are estimates from calculations based on a number of assumptions, such as no change in metabolic rate with increasingly energetic breathing.

Because the stimulator of the present invention is a new discovery, no explanation of how it works has been found in the scientific literature. The numbers in Table I and the following discussion are necessarily somewhat speculative, but nevertheless provide an explanation of the manner in which the invention works.

As shown in the above Table I, assuming no change in metabolic rate, the same amount of $CO_2$ is spread over progressively larger minute ventilation volumes as the chamber 14 size is increased. The consequence of this is that the $PCO_2$ in progressively larger chambers falls and the user's alveolar $PO_2$ rises. Thus, the user's average alveolar $PCO_2$ falls to very low levels even though arterial $PCO_2$ remains normal. A large difference between arterial $PCO_2$ and alveolar $PCO_2$ is the hallmark of a high ventilation/perfusion ratio V/Q. Clearly, the enormous increase in ventilation (V) provided by a large trap is not matched by an increase in perfusion (Q), hence the high V/Q ratio. This suggests that if perfusion were to increase two or threefold without a concomitant increase in $CO_2$ production there would be a drastic reduction in the stimulation provided by a stimulator.

Hypoxia at high altitude causes a reflex stimulation of cardiac output in the unacclimatized individual. However, cardiac output, and hence pulmonary perfusion, only rises by 20 or 30 percent. Furthermore, utilizing a stimulator at altitudes of 20,000 feet or so should prevent hypoxia. Thus, it is unlikely that a rise in Q at high altitude will reduce the effectiveness of the stimulator.

A situation where a two or threefold increase in Q might be desirable is in the treatment of carbon monoxide poisoning. Cardiac output could possibly be increased threefold by pharmacologic means. The new minute ventilation resulting from a lower V/Q ratio can probably be calculated thus. A subject with a resting minute ventilation of 6 L/min and a tidal volume of 500 cc has this tidal volume because it provides the best match between ventilation and perfusion. If resting Q increased threefold, then resting V should also increase threefold to maintain the same V/Q ratio. Thus, if the resting alveolar ventilation of 350 cc (500 cc tidal volume minus 150 cc dead space) is multiplied by 3 the new resting tidal volume will be 1.2 L (3×350+150). The number of respirations per minute is found simply by dividing the resting alveolar ventilation of 4.2 L/min by the new alveolar tidal volume of 1.02 L=4.0 respirations/min. A 5 liter chamber 14 which would ordinarily provide a stimulated ventilation of 66 L/min would now only supply (5+1.2)×4= 24 L/min. Nevertheless, this is still a fourfold increase in ventilation over the resting level, and a 5 liter trap in conjunction with 100% oxygen should be a very effective treatment for carbon monoxide poisoning.

Figure 9:
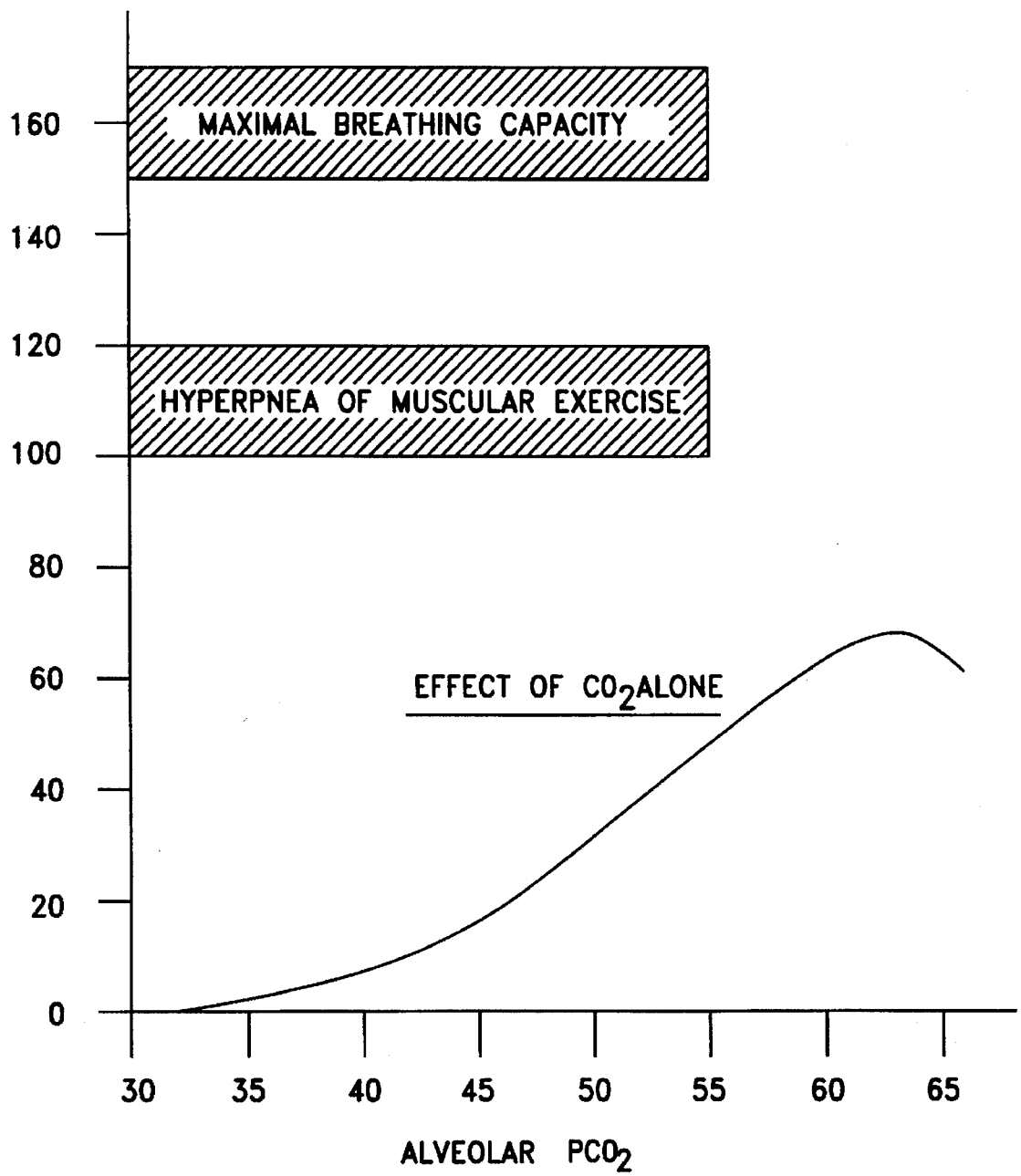
FIG. 9 is a graph showing the relationship of hypernea due to exercise and that caused by breathing CO2 enriched air.

FIG. 9 compares the increased breathing caused by muscular exercise to that caused by breathing CO2 enriched air. As can be seen, muscular exercise produces minute ventilations more than double that of breathing CO2. The present invention produces minute ventilations as high or higher caused by maximal exercise.

Firm experimental evidence, obtained in a high altitude flight in an unpressurized turbocharged airplane, demonstrated that the stimulator worked as predicted. FIG. 10 displays this evidence as a family of curves plotting arterial hemoglobin saturation (SaO2) against altitude, breathing unassisted and with various size traps or mixing chambers. The subject's arterial hemoglobin saturation (SaO2) was continuously recorded by a pulse oximeter from sea level to 24,000 feet. Measurements were made at each thousand foot level breathing without assistance and with four different size traps or mixing chambers: 1 quart, 2 quart, 1 gallon, and 2 gallon. The two gallon trap was used at the highest altitudes and continuously during the descent to 10,000 feet.

The present invention does not increase the $CO_2$ content of the blood beyond its eucapnic level and is not applicable for treating hyperventilation syndromes or the specialized application described in U.S. Pat. Nos. 4,508,116 and 4,628,926 to Duncan. However, it should be far superior to the known respiratory exercisers, such as those disclosed in U.S. Pat. No. 3,455,294 to Adler and U.S. Pat. No. 4,275,722 to Sorensen. It is anticipated that this and other medical uses of the device will probably be just as important as the high altitude applications.

The present invention may advantageously be used to solve problems that still exist in the state of the art in a wide variety of fields.

For example, rebreathing devices in accordance with the present invention are particularly well suited for a variety of aviation applications. Oxygen and pressurized cabins have not solved all of the problems posed by hypoxia in aviation. There is a very large fleet of general aviation aircraft and only a small percentage have pressurized cabins. The great majority of the unpressurized aircraft probably fly without oxygen. Although these pilots generally fly below 10,000 feet, occasionally because of strong updrafts or emergency conditions, they may fly at much higher altitudes where hypoxia can become a real hazard. The FAA (FAR Part 91.211) dictates that the minimum flight crew must use oxygen on flights of over 30 minutes duration between 12,500 and 14,000 feet of cabin pressure altitude. Above 14,000 feet, the crew must use oxygen at all times, and above 15,000 feet, everyone in the plane must be provided with supplemental oxygen. However, heavy smokers and many older pilots can become significantly hypoxic and require oxygen at altitudes as low as 10,000 feet.

There is also the problem of low altitude hypoxia. Even at altitudes of 5,000 to 10,000 feet hypoxia can pose a subtle danger. At the very least it adds to the strain and fatigue of flying, but it also interferes with vision, hearing, and cognition. Because of this the FAA recommends the use of oxygen from the ground up for night flying. The accident rate for general aviation aircraft is appallingly high, almost entirely due to pilot error. Otherwise intelligent, reasonably well trained pilots often show poor judgment. How much of this poor judgment is due to the subtle effects of low altitude hypoxia is a matter of conjecture.

Airline pilots possibly also experience low altitude hypoxia, since airliners are pressurized at up to 8,000 feet cabin altitude, without any apparent adverse effects. However, airline flying is highly routine and automated—the airplanes literally fly and navigate themselves—and all flights are under instrument flight rules with strict ground control. Even so, many airlines require their pilots to use supplemental oxygen prior to landing to sharpen vision and improve cognitive ability.

Even in airline flying there may be room for improvement particularly in emergency situations. With loss of cabin pressure at high altitude, emergency oxygen masks are automatically deployed. However, the oxygen supply is typically only sufficient to provide time to fly to a lower altitude, but not sufficient to permit sustained flying at higher altitudes. There could be a real safety factor, in terms of avoiding weather or for fuel economy, if the pilot had the option to fly at 20,000 feet instead of lower altitudes.

In a sea level portion of their study, Harvey, et al., in "Effect of Carbon Dioxide in Acute Mountain Sickness: A Rediscovery," 1988 Lancet, reported that breathing 5% oxygen/95% nitrogen rendered subjects unconscious with grossly abnormal changes in the electroencephalogram. The addition of 5% CO2 gas (i.e., 5% $CO_2$+5% $O_2$+90% N2) restored consciousness and returned the EEG to normal. A mixture of 5% oxygen has a $PO_2$ of only 38 mm Hg. Before 1900, Angelo Mosso used $CO_2$ mixtures at pressures as low as 250 torr (about 8800 m or almost 29,000 feet) in a hypobaric chamber as reported in "Life of Man on the High Alps," 1898 London. This would suggest that $CO_2$ enriched air works almost as well as breathing 100% oxygen. However, although everyone agrees carbon dioxide has a definite altitude lowering effect, more recent studies have called into question the findings from prior uncontrolled trials. A study by Bartsch, et al., entitled "Comparison of carbon-dioxide enriched, oxygen-enriched, and normal air in treatment of acute mountain sickness," 1990 Lancet, completely contradicts Harvey and other prior studies and concludes there is no usefulness of carbon dioxide treatment for acute mountain sickness. A precise study under laboratory conditions using a hypobaric chamber by Maher in 1975 showed that an altitude of 4000 meters (13,124 feet) with subjects breathing 3.8% carbon dioxide was equivalent to an altitude of 3,500 meters (11,484 feet) for subjects breathing ordinary air, an altitude lowering effect of only 1,641 feet. Referring once again to FIG. 10, note that the 2 gallon trap produced essentially sea level $SaO2$'s up to 16,000 feet. This is an altitude lowering effect of 16,000 feet, an order of magnitude greater than that produced by carbon dioxide.

Most light planes rarely fly above 20,000 feet, indeed most cannot even climb that high. The availability of the stimulator of the present invention should be a valuable backup in case of oxygen system failure, or for emergency conditions in aircraft without oxygen. It should also be the perfect solution to low altitude hypoxia, and might even give airliners an added safety factor in case of loss of cabin pressure.

Another application of the present invention is in mountaineering. For more than half a century, experts have known that inhaled $CO_2$ might be useful in assisting breathing during climbing to great altitudes. It would be reasonable to expect that unacclimatized climbers would receive the most benefit. The present invention permits a mountaineer to quickly go from sea level to a high altitude. This should permit unprecedented freedom of movement and scheduling.

The stimulator of the present invention should also be of benefit to acclimatized climbers, permitting higher altitudes with less hypoxia. Even if a climber did not wish to wear a mask while climbing, the stimulator, by abolishing Cheyne-Stokes respiration, should make sleep safer and more restful. The old mountain climbing adage, "climb high, sleep low" would no longer be necessary.

A variety of methods in the field of medicine can be advantageously performed using the stimulator of the present invention. In the field of medicine, there are a number of clinical situations where a great increase in pulmonary ventilation would be highly beneficial, but at present, because of the unavailability of $CO_2$ mixtures, this is impossible due to hypocapnia. The following are some examples.

Acute Mountain Sickness (AMS). AMS can progress to high altitude pulmonary edema (HAPE) or high altitude cerebral edema (HACE). Both HAPE and HACE are grave medical conditions which continue to cause fatalities. The ready availability of an stimulator could be life saving.

In accordance with a further aspect of the present invention, there is provided a method of treating Carbon Monoxide Poisoning. The treatment objective is to remove carbon monoxide from the blood stream and body as quickly and thoroughly as possible. However, the affinity of hemoglobin for carbon monoxide is 210 times its affinity for oxygen. To speed up the otherwise very slow release of carbon monoxide from carboxyhemoglobin, a mass action effect is required. For this reason, hyperbaric oxygen is especially valuable. However, for immediate treatment and for treatment during transport to a hyperbaric oxygen facility, oxygen supplied through the stimulator of the present invention would greatly increase ventilation and accelerate the elimination of carbon monoxide. It would also be advantageous to use a carbon monoxide absorbing filter to prevent rebreathing carbon monoxide from the chamber 14. Additionally, it might be desirable to increase pulmonary perfusion by the pharmacologic stimulation of cardiac output. With these measures it is possible that the stimulator might be able to replace hyperbaric oxygen as treatment of choice for carbon monoxide poisoning.

Mechanical Ventilation can also potentially be enhanced by a use of a breathing apparatus in accordance with the present invention. Just as in ordinary breathing, the rate of mechanical ventilation is limited by hypocapnia. The stimulator of the present invention would permit much more flexibility. Greatly increased ventilation might permit the use of lower concentrations of oxygen and lower positive end expiratory pressure (PEEP), thereby avoiding possible oxygen toxicity and complications of high PEEPs.

There is further provided a method of inducing Breathing Exercise for Patients Unable to Exercise, comprising breathing through a breathing device of the present invention for an exercise inducing period of time. Bedridden patients, or patients with angina pectoris, pulmonary disease, congestive heart failure, arthritis, and the like, may get little or no exercise. Not only do these patients develop severe deconditioning of their skeletal muscles, but their respiratory muscles are also affected. This has well known adverse consequences when the respiratory system is put under stress, such as with pneumonia or major surgery. In extremely compliant and strongly motivated people, special exercises may theoretically improve respiratory muscle strength and endurance, but as a practical matter it is unlikely these exercises accomplish anything in other patients, and particularly sick elderly patients.

The stimulator of the present invention, however, can provide very vigorous breathing which, being automatic and involuntary, requires no compliance or motivation. This increased breathing can be continued for one or more preset intervals up to the fatigue limits of the patient. Furthermore, because breathing is so efficient, even a high ventilatory rate can be sustained at only a small metabolic cost.

As an example, a coronary patient who develops angina with moderate walking, could probably sustain a ventilatory rate equivalent to fast running without discomfort. If over a period of time such as several weeks the patient could work up to an hour of this level of breathing a day, there should be substantial improvement in vital capacity and respiratory muscle strength and endurance. This should greatly improve the patient's chances of going through coronary bypass surgery without pulmonary complications. Thus, the stimulator of the present invention offers the possibility of substantially improving respiratory function and well being in a very large group of debilitated patients, something that is completely unobtainable at the present time.

A method of respiratory training of healthy humans, such as in preparation for any of a variety of athletics is also provided in accordance with the present invention. For many athletes, the most difficult, distressing, and performance limiting factor is the extreme dyspnea that develops with maximal effort. This is probably both a physiological and psychological barrier. There is evidence that, with training, athletes can inure themselves to dyspnea.

Although it is difficult to know what measures are available to world class athletes in sophisticated proprietary and government training programs, the great majority of athletes are limited to wind sprints and interval training. These exercises are extremely fatiguing, of short duration, and when overdone can lead to staleness and injury. Thus the amount of respiratory training these athletes receive is really quite limited.

The ability to uncouple respiration from exercise that the stimulator of the present invention provides, should make it possible to selectively train and condition the respiratory system. The device, especially in combination with mild or moderate exercise, could provide extended periods of severe dyspnea with only a very moderate expenditure of energy.

A number of additional potential uses of the stimulator of the present invention include facilitating smoking cessation and treatment of obesity. Successfully stopping smoking involves overcoming two addictions, a physiological one and an emotional one. For many heavily addicted smokers the physiological addiction is an insurmountable barrier. However, in the first few days of stopping smoking, a great deal of the often overwhelming urge to smoke, experienced as the intense desire to deeply inhale a cigarette, may simply be a matter of air hunger. Possibly the respiratory center is hypoactive after years of chronic stimulation by nicotine. In any case, the urge for a cigarette can often be dispelled by a few deep breaths. However, for many smokers, this is difficult both to do and to remember. The use of an stimulator of the present invention for several days would completely eliminate the air hunger and might be a very useful stop smoking aid for the heavily addicted smoker.

Lack of exercise may be a more important cause of obesity than overeating. Certainly, if everyone walked ten miles a day (or the equivalent) almost everyone could eat to satiety and almost everyone would be thin. However, this is probably ten times more exercise than most people are willing to contemplate much less do, and more than three times as much exercise as most doctors are willing to recommend to their patients.

In all fairness to overweight people, exercise becomes progressively more difficult, uncomfortable and discouraging the older and fatter an individual becomes. For the average middle aged obese person, exercycles and rowing machines are impossible, high impact aerobics out of the question, low impact aerobics the equivalent of no aerobics, and even walking more than a block or two may prove too arduous and painful. Thus, if a person in this predicament could do something to lose weight that he or she does all the time anyway, such as breathing, it might represent a new and useful alternative.

Even though breathing is extremely efficient, it nevertheless requires work. A small amount of work performed over a long period of time seems just as effective in causing weight loss as a large amount of exercise in a short time. For example, the resting tremor of Parkinson's Disease is very low level exercise, yet because it exists during all waking hours it uses a lot of energy and these patients lose weight. Preliminary estimates suggest that a ventilatory rate that requires the same caloric expenditure as one mile per hour walking would not be unreasonable. The ideal would be to go to sleep and wake up eight hours later having done the equivalent of eight miles of walking.

A variety of different models of the breathing stimulator will be apparent to one of skill in the art in view of the disclosure herein, depending on the desired application. All designs incorporate a carbon dioxide trap, which can be integrated in a face mask 36, as shown in FIG. 4, or contained in a separate housing 12, as shown in FIG. 1. The face mask 36 design can probably accommodate a trap volume of up to 2.5 L, which would multiply resting ventilation by a factor of up to 6. This might be satisfactory for most aviation, mountaineering, and medical applications.

For aviation or mountain climbing use, in order to minimize facial injury in case of impact, the mask 36 should be made of soft but fairly firm and durable rubber. The mask 36 can be part of a helmet 54 which would include earphones 56 and a microphone 58 for ease of communication, as can be seen in FIG. 5. A clear silicone rubber version might be preferable for other applications, such as for stopping smoking. A very light plasticized paper version, which would fold accordion style 52 into a small flat space, might be suitable for one time emergency use on airliners, as can be seen in FIG. 3.

A tank version 10 (as shown in FIG. 1) of the breathing stimulator would be useful for higher volume traps, such as might be necessary for athletic training, weight loss, treatment of carbon monoxide poisoning, and very high altitude applications. The tank 10, connected by tube 20 (as short as possible) to a face mask (not shown), can be of telescoping design 28, as can be seen in FIG. 6, thereby allowing great flexibility in the choice of trap volume and consequent respiratory stimulation.

For specialized applications certain additional features can be incorporated. At low altitudes in urban smoggy areas, anyone who breathes at many times the resting rate for a prolonged period would be subjecting the respiratory system to a high load of atmospheric pollutants. Thus, for this type of application a special smog filter 38 with valves 40, 42 may be used as shown in FIG. 7. For treatment of carbon monoxide poisoning a special filter for removal of carbon monoxide would be advantageous. To use the trap with oxygen, simple flutter valves 46 would be required as shown in FIG. 8. For use with mechanical ventilation, a fan (not shown) may be required in the mixing chamber to ensure adequate mixing of inhaled and exhaled air in the chamber.

The stimulator of the present invention does everything that $CO_2$/air mixtures can do. However, it has enormous advantages over $CO_2$ mixtures. In probable order of importance these are as follows:

The breathing stimulator is safe to use. Because the source of the $CO_2$ is the user's own respiration, there is no possibility of human error or equipment failure leading to accidental asphyxiation or $CO_2$ narcosis. As long as the physiological mechanism stimulates respiration to maintain arterial $PCO_2$ within normal limits, there should be no complications from hypercapnia. This would mean that the breathing stimulator could be used for prolonged periods (24 hours or more) without loss of sensitivity and responsiveness to stimulation and with no fear of developing pulmonary hypertension.

Physiological stimulation is also provided. The breathing stimulator provides physiological stimulation, akin to exercise, and therefore, has major advantages over $CO_2$ mixtures. It provides stimulation without adverse effects right up to maximum voluntary respiration and thus provides complete uncoupling or disassociation of ventilation from exercise, which should make it a useful ergogenic training device.

The stimulator also provides an unlimited supply of $CO_2$ because the source is the user's own respiration. The concentration of $CO_2$ in the trap is also controlled automatically and involuntarily by the user's respiratory system.

The breathing stimulator also has complete portability, and can be designed to weigh only a few ounces, and can be used under all conceivable conditions. The breathing stimulator will also be only a fraction of the cost of any possible method for delivering a $CO_2$/air mixture.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention.

I claim:

1. A respiratory stimulator, including a rigid mixing chamber where the contents of the chamber include exhaled air and fresh air which are mixed together by the breathing of a user, said chamber not varying substantially in volume in response to exhalation and inhalation of the user, a breathing port in the chamber which provides communication between the user and the mixing chamber, upon exhalation of the user, exhaled air entering the chamber as a jet stream to create turbulence within the chamber and being entrapped in the chamber and mixed with the contents of the chamber, and, upon inhalation of the user, a portion of the contents of the chamber being drawn through the breathing port, and a vent opening structure in the chamber for providing communication between the mixing chamber and the atmosphere, upon exhalation of the user, a portion the contents of the chamber substantially equal to the volume of air exhaled by the user being exhausted to the atmosphere through the vent opening structure, and upon inhalation of the user, fresh air as a jet stream substantially equal to the volume of air inhaled by the user being introduced into the chamber through the vent opening structure, said vent opening structure having a sufficiently large cross-sectional area to allow that portion of the contents of the chamber being exhausted to flow freely out of the chamber as the user exhales into the chamber without substantially increasing the pressure within the chamber yet being sufficiently restrictive to promote turbulent mixing in the chamber of the contents of the chamber and fresh air drawn into the chamber upon inhalation.

2. The respiratory stimulator of claim 1 where the pressure within the chamber upon exhalation or exhalation does not change more than 15 centimeters of water either above or below ambient atmospheric pressure.

3. The respiratory stimulator of claim 2 where the volume of the chamber ranges between 1.5 and 20 liters.

4. The respiratory stimulator of claim 1 where cross-sectional area of the vent opening structure ranges between 0.75 and 20 square centimeters.

5. The respiratory stimulator of claim 1 where the breathing port of the chamber is enlarged into an open end of a face mask that fits over the mouth, the mouth and nostrils, or the entire face of the user.

6. The respiratory stimulator of claim 5 where face mask has a collapsed position and an extended position.

7. The respiratory stimulator of claim 1 including a breathing passageway structure for placing the breathing port in communication with the mouth or nostrils, or both, of the user, said breathing passageway structure having a volume which is less than 500 cubic centimeters.

8. The respiratory stimulator of claim 1 where the chamber includes a filter.

9. The respiratory stimulator of claim 1 where the chamber is in communication with a supply of oxygen gas.

10. A respiratory stimulator for increasing the minute ventilation of a user to a predetermined level substantially above the minute ventilation of user when breathing normally during resting, including a rigid mixing chamber in which exhaled air is mixed with fresh air and which does not vary in volume in response to inhalation and exhalation of a user, said chamber having a predetermined capacity based on said predetermined level of increased minute ventilation, a breathing port in the chamber which provides communication between the user and the mixing chamber, the exhaled air entering the chamber through the breathing port being entrapped in the chamber and mixed with fresh air in said chamber, a breathing passageway structure for placing the breathing port in communication with the mouth or nostrils, or both, of the user, said breathing passageway structure having a volume which is less than 500 cubic centimeters, and a vent opening structure in the chamber through which, upon exhalation, a portion of the exhaled air/fresh air mixture in the chamber equal to the volume of air exhaled by the user is exhausted to the atmosphere and through which, upon inhalation, fresh air equal to the volume of air inhaled by the user is introduced into the chamber, said vent opening structure having a sufficiently large cross-sectional area to allow the exhaled air/fresh air mixture to flow freely out of the chamber as the user exhales into the chamber without substantially increasing the pressure within the chamber yet being sufficiently restrictive to promote mixing in the chamber of fresh air with exhaled air.

\* \* \* \* \*